United States Patent
el Kaliouby et al.

(10) Patent No.: US 10,796,176 B2
(45) Date of Patent: Oct. 6, 2020

(54) PERSONAL EMOTIONAL PROFILE GENERATION FOR VEHICLE MANIPULATION

(71) Applicant: Affectiva, Inc., Boston, MA (US)

(72) Inventors: Rana el Kaliouby, Milton, MA (US); Abdelrahman N. Mahmoud, Somerville, MA (US); Seyedmohammad Mavadati, Watertown, MA (US); Gabriele Zijderveld, Somerville, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 16/173,160

(22) Filed: Oct. 29, 2018

(65) Prior Publication Data

US 2019/0073547 A1 Mar. 7, 2019

Related U.S. Application Data

(63) Continuation-in-part of application No. 15/875,644, filed on Jan. 19, 2018, now Pat. No. 10,627,817, (Continued)

(51) Int. Cl.
*G06K 9/00* (2006.01)
*G08G 1/01* (2006.01)
(Continued)

(52) U.S. Cl.
CPC ............ *G06K 9/00845* (2013.01); *A61B 5/18* (2013.01); *B60W 40/08* (2013.01); (Continued)

(58) Field of Classification Search
USPC .......................................................... 701/36
See application file for complete search history.

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP          08115367      7/1996
KR   10-2005-0021759 A   3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Tyler D Paige
(74) *Attorney, Agent, or Firm* — Adams Intellex, PLC

(57) ABSTRACT

Personal emotional profile generation uses cognitive state analysis for vehicle manipulation. Cognitive state data is obtained from an individual. The cognitive state data is extracted, using one or more processors, from facial images of an individual captured as they respond to stimuli within a vehicle. The cognitive state data extracted from facial images is analyzed to produce cognitive state information. The cognitive state information is categorized, using one or more processors, against a personal emotional profile for the individual. The vehicle is manipulated, based on the cognitive state information, the categorizing, and the stimuli. The personal emotional profile is generated by comparing the cognitive state information of the individual with cognitive state norms from a plurality of individuals and is based on cognitive state data for the individual that is accumulated over time. The cognitive state information is augmented based on audio data collected from within the vehicle.

28 Claims, 14 Drawing Sheets

Related U.S. Application Data which is a continuation-in-part of application No. 15/273,765, filed on Sep. 23, 2016, now abandoned, which is a continuation-in-part of application No. 14/796,419, filed on Jul. 10, 2015, now abandoned, which is a continuation-in-part of application No. 14/460,915, filed on Aug. 15, 2014, and a continuation-in-part of application No. 14/328,554, filed on Jul. 10, 2014, now Pat. No. 10,111,611, which is a continuation-in-part of application No. 13/153,745, filed on Jun. 6, 2011, now abandoned, which is a continuation-in-part of application No. 13/153,745, filed on Jun. 6, 2011, now abandoned.

(60) Provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/844,478, filed on Jul. 10, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | | |
|---|---|---|
| *B60W 40/08* | | (2012.01) |
| *A61B 5/18* | | (2006.01) |
| *G06Q 30/02* | | (2012.01) |
| *H04L 29/08* | | (2006.01) |
| *G08G 1/0967* | | (2006.01) |
| *G06K 9/62* | | (2006.01) |
| *G06N 3/04* | | (2006.01) |
| *G06N 3/08* | | (2006.01) |
| *G10L 25/48* | | (2013.01) |

(52) U.S. Cl.
CPC ..... *G06K 9/00302* (2013.01); *G06K 9/00315* (2013.01); *G06K 9/6273* (2013.01); *G06N 3/0445* (2013.01); *G06N 3/0454* (2013.01); *G06N 3/084* (2013.01); *G06Q 30/0255* (2013.01); *G08G 1/0112* (2013.01); *G08G 1/0129* (2013.01); *G08G 1/096716* (2013.01); *G08G 1/096725* (2013.01); *G08G 1/096741* (2013.01); *G08G 1/096775* (2013.01); *H04L 67/22* (2013.01); *H04L 67/306* (2013.01); *G10L 25/48* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |

(56) References Cited

U.S. PATENT DOCUMENTS

| | | |
|---|---|---|
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,487,772 B1 | 7/2013 | Higgins |
| 8,522,779 B2 | 9/2013 | Lee et al. |
| 8,527,146 B1* | 9/2013 | Jackson ............ B60W 50/0098 701/36 |
| 8,600,120 B2 | 12/2013 | Gonion et al. |
| 8,640,021 B2 | 1/2014 | Perez et al. |
| 8,738,523 B1 | 5/2014 | Sanchez et al. |
| 8,947,217 B2 | 2/2015 | Moussa et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0072952 A1* | 6/2002 | Hamzy ................ G06Q 30/02 705/7.29 |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0179229 A1* | 9/2003 | Van Erlach ........... G06F 1/1626 715/744 |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1* | 1/2006 | Brockway ................ A61B 5/18 180/272 |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1* | 11/2009 | Moon ................ G06K 9/00335 382/118 |
| 2009/0299840 A1 | 12/2009 | Smith |
| 2010/0004977 A1* | 1/2010 | Marci ..................... A61B 5/16 705/7.32 |
| 2010/0023393 A1* | 1/2010 | Costy ..................... G06Q 30/02 705/14.43 |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0257985 A1* | 10/2011 | Goldstein ........... G06F 16/3334 705/1.1 |
| 2011/0263946 A1 | 10/2011 | el Kaliouby et al. |
| 2012/0109452 A1 | 5/2012 | Autran et al. |
| 2012/0290950 A1* | 11/2012 | Rapaport .............. H04L 51/32 715/753 |
| 2012/0324491 A1 | 12/2012 | Bathiche et al. |

(56) References Cited

U.S. PATENT DOCUMENTS

| | | |
|---|---|---|
| 2013/0023337 A1 | 1/2013 | Bowers et al. |
| 2013/0116587 A1 | 5/2013 | Sornmo et al. |
| 2013/0197409 A1 | 8/2013 | Baxter et al. |
| 2013/0204455 A1 | 8/2013 | Chia et al. |
| 2014/0100971 A1* | 4/2014 | Klearman ......... G06Q 30/0641 705/15 |
| 2014/0171752 A1 | 6/2014 | Park et al. |
| 2014/0172910 A1 | 6/2014 | Jung et al. |
| 2014/0218187 A1 | 8/2014 | Chun et al. |
| 2015/0258995 A1 | 9/2015 | Essers et al. |
| 2016/0104486 A1 | 4/2016 | Penilla et al. |
| 2017/0003784 A1 | 1/2017 | Garg et al. |
| 2018/0174139 A1* | 6/2018 | Arora ................ G06Q 20/367 |
| 2018/0260845 A1* | 9/2018 | Peterson ........... G06Q 30/0261 |
| 2019/0073547 A1* | 3/2019 | el Kaliouby ........ G06N 3/0445 |
| 2019/0110103 A1* | 4/2019 | el Kaliouby ........ G08G 1/0112 |
| 2019/0268660 A1* | 8/2019 | el Kaliouby ....... H04N 21/4223 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

* cited by examiner

PERSONAL EMOTIONAL PROFILE GENERATION FOR VEHICLE MANIPULATION

RELATED APPLICATIONS

This application claims the benefit of U.S. provisional patent applications "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State Engineering" Ser. No. 62/679,825, filed Jun. 3, 2018.

This application is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicle Manipulation using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Personal Emotional Profile Generation" Ser. No. 14/328,554, filed Jul. 10, 2014, which claims the benefit of U.S. provisional patent applications "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014.

The patent application "Personal Emotional Profile Generation" Ser. No. 14/328,554, filed Jul. 10, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to cognitive state analysis and more particularly to personal emotional profile generation for vehicle manipulation.

BACKGROUND

An individual's emotions are an important component of who they are. A person's response to stimuli can have a profound impact on the mental states they experience. The mental state of an individual can run a broad gamut from happiness to sadness, from contentedness to worry, and from excitement to calm. These mental states are experienced in response to everyday events such as frustration during a traffic jam, boredom while standing in line, and impatience while waiting for a cup of coffee.

Individuals who are able to understand their emotional states have the option to use the information to accommodate their current abilities or limitations. Many mental states, such as frustration, confusion, disappointment, boredom, disgust, and delight, can be identified and related to behavioral patterns. When confronted with unpleasant mental states, individuals can respond with cravings for pleasure, comfort, reward, or enjoyment. On perhaps an even more visible scale, individuals can often be observed evidencing a collective emotional response, such as responding with fear and anxiety after witnessing a catastrophe or responding with happy enthusiasm when their sports team obtains a victory. When an individual is aware of his or her mental states, he or she is better equipped to realize his or her own abilities, cope with the normal stresses of life, work productively and fruitfully, and make a contribution to his or her community.

People undertake travel for a wide range of purposes. Travel, which usually involves moving one or more people from one location to another, can be undertaken for financial reasons such as commuting to and from work or school, for personal reasons such as pleasure, relaxation, or discovery, or for exercise, to name only a few. Travel can also result from more sinister events such as war, famine, or displacement. Depending on the purpose of the travel and the modes of transportation available, people choose a mode of transportation based on convenience, availability, or cost. The modes of transportation include ground transportation, water transportation, and air transportation. Ground transportation can be accomplished on foot, by animal, or by vehicle such as a bicycle, an automobile, a van, a bus, or a train. Water transportation can include using a personal vehicle such as a raft, canoe, or kayak, a public vehicle such as a ferry or a ship, among others. Air transportation can be accomplished using an airship or airplane. Whichever mode of transportation is chosen by a person, the mode most often involves a vehicle.

People spend a tremendous amount of time in vehicles. Whether waiting for a vehicle, traveling in the vehicle, attempting to park the vehicle, waiting in security lines to get on a vehicle, among many other travel-related activities, substantial portions of time are committed to vehicular travel. Typical vehicle-related travel events include the daily commute; taking the kids to athletic practices, musical instrument lessons, or debate club; taking the pets to the veterinary clinic; shopping for food or household items; traveling; or any of the other common activities that require transportation, and people use a variety of vehicles to meet their transportation needs. Traveling in a vehicle is time consuming at best, and at worst, boring, frustrating, and irritating. Rush hour traffic, accidents, inclement weather, and poorly maintained roads, among other situations, further complicate automotive transportation. The difficulties of transportation are also compounded by operating an unfamiliar vehicle, traveling in an unfamiliar city, and even having to remember to drive on the opposite side of the road in a construction zone or when traveling in some foreign countries. Sadly, these transportation realities can have catastrophic consequences. Irritated operators of vehicles can experience road rage and other antisocial behaviors, and bored, sleepy, impaired, distracted, or otherwise inattentive drivers can cause vehicular accidents and injury to themselves, pedestrians, bicyclists, animals, and property. Many such vehicle-related travel events can complicate vehicle travel and require additional resources from community service organizations such as police, fire departments, and emergency medical treatment providers.

SUMMARY

Analysis of mental states can be performed to develop a mental state profile for an individual or group of individuals. The mental states can include emotional states, cognitive states, and/or physiological states. Example mental states include frustration, concentration, confusion, disappointment, hesitation, cognitive overload, focusing, engagement, attention, boredom, exploration, confidence, trust, delight, disgust, skepticism, doubt, satisfaction, excitement, laughter, calmness, stress, happiness, sadness, smiling, frowning, curiosity, and numerous others. Mental state profile information can be used to display patterns and norms for the individual or a group, and can aid in understanding consumer behavior, tailoring products to closer match a user's desires, and improving websites and interfaces to computer programs. A computer-implemented method for mental state analysis is disclosed comprising: obtaining cognitive state data from an individual within a vehicle, wherein the cognitive state data is extracted, using one or more processors, from facial images of the individual that are captured as the individual responds to stimuli; analyzing the cognitive state data extracted from facial images to produce cognitive state information; categorizing, using one or more processors, the cognitive state information against a personal emotional profile for the individual; and manipulating the vehicle, based on the cognitive state information, the categorizing, and the stimuli.

In embodiments, the personal emotional profile is generated by comparing the cognitive state information of the individual with cognitive state norms from a plurality of individuals. In embodiments, the personal emotional profile is generated based on cognitive state data for the individual that is accumulated over time. In embodiments, the personal emotional profile is further generated based on two or more vehicle journeys by the individual. In embodiments, at least two of the two or more vehicle journeys are accomplished in two or more vehicles. Some embodiments further comprise augmenting the cognitive state information based on audio data collected from within the vehicle, wherein the audio data is collected contemporaneously with the facial images. In embodiments, the cognitive state data that was analyzed is based on intermittent obtaining of images that include facial data.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
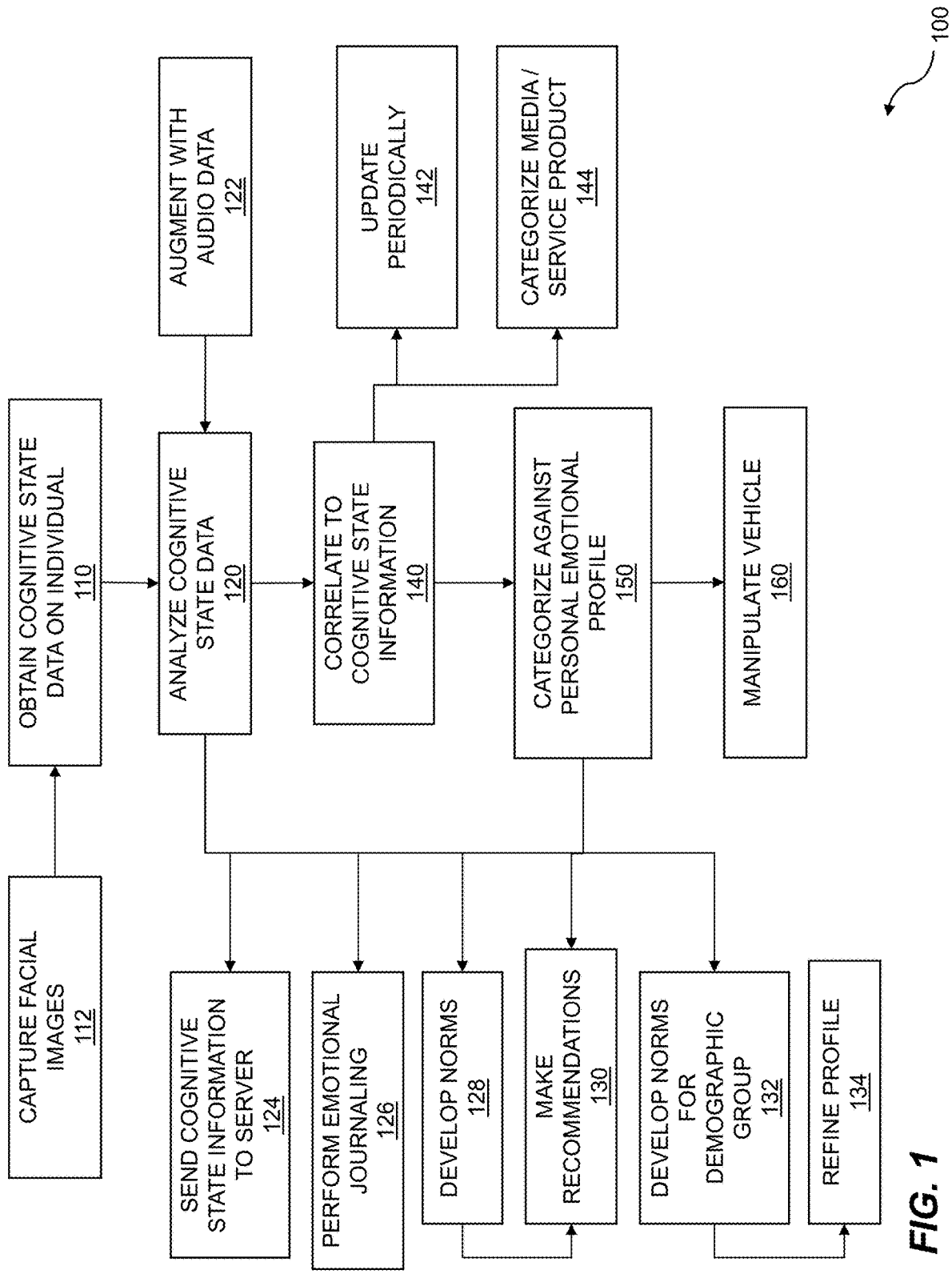
FIG. 1 is a flow diagram for personal emotional profiling in a vehicle.

People exhibit and communicate a wide range of emotions in their daily lives. These emotional states are experienced in response to everyday events and, when identified as a pattern, can create an emotional identity associated with a particular person or group of people. Changes in the emotional state of an individual can occur quickly and might not be easily recognized by the individual, often resulting in situations where the individual has difficulty summarizing and describing his or her emotional state. Providing an assessment of an emotional state can assist the individual with decision-making, activity selection, activity scheduling, and other tasks. When the assessment describes an emotional characteristic or pattern, the data can allow useful analysis and tailoring of material for the person or group of people.

To this end, a personal emotional profile, which includes a summary or analysis of data representing a person's distinctive features or characteristics, can be created. These characteristics can include the emotional state of an individual at a moment in time or over a period of time. The profile can include distinctive habits, attitudes, qualities, behaviors, and emotional traits of an individual or groups of individuals. The profile can provide the individual, or group of individuals, with perspective and insight about their general emotional characteristics, or their emotional state in response to certain activities or behaviors. In addition, the profile can be used to track reactions of a person or people to certain stimuli. For instance, in a certain embodiment, a profile identifies the number of times that a person has laughed during a certain time period, providing a way to track the responsiveness of the person to humor. Such laugh tracking could be used to identify receptiveness to general or specific types of humor, or to provide the individual with information when certain milestones are reached during the day—10,000 laughs, for example. Additionally, emotional response tracking could be used to gauge and analyze readiness to react to emotional scenes in media. In some cases, certain reactions could be incentivized. For example, game points could be earned and stored within a profile based on certain emotional responses. Some examples of such incentivizing could include giving points to the first individual to laugh when exposed to a certain joke, or to the first individual to evidence emotional distress when exposed to a distressing situation. Other types of scoring could likewise be analyzed and recorded as part of the emotional profile. In addition, a personal emotional profile generated while an individual is an occupant, driver, or passenger, of a vehicle can be especially useful in helping to control or manipulate the vehicle, as well as providing insight into entertainment options, occupant interaction compatibility, climate options, and so on. The personal emotional profile can be generated using video input of the occupants, audio input of the occupants, or a combination of video and audio inputs of the occupants. Video and audio from outside the vehicle can also play a role in determining the personal emotional profile, the stimuli to which an occupant is responding, ambient conditions within and without the vehicle, and so on. For example, bright sunlight on the outside of the vehicle may be an important factor for vehicle drivability, comfort, safety, etc.

Analysis of an individual's emotional state can be used to provide feedback to the individual about the status of his or her well-being. The feedback can be used to create a personal emotional profile of the individual. The emotional states of a plurality of individuals can be correlated and compared to a predefined group of individuals. Various attributes can be associated and used to define categories of individuals with similar emotional profiles. The analysis can take place on a computer with which the user is interacting. This profile information can be combined with additional information about the individual, such as demographic information, to create a more comprehensive outline and summary of the emotional state of the individual. A category from an emotional profile can be used to further enhance the demographic profile. The profile can be used to extrapolate behavior, predict future reactions to certain events, or inform a social profile of an individual. This personal emotional profile can be used to make recommendations for different activities, and can include recommendations for activity performance based upon time of day, a period of time during the day, or other calendar-based scheduling. The profile can also be included in an aggregated analysis along with a plurality of people's emotional profiles allowing for activity recommendations.

A personal emotional profile can be developed by evaluating facial expressions, hand gestures, and physiological conditions exhibited by an individual. For example, the human face is a powerful channel for communicating a wide variety of emotional states. The general expressiveness of an individual as they view input stimuli can be analyzed to determine an emotional state. A camera or another facial recognition device can be used to capture images of an individual's face, and software can be used to extract and interpret laughs, smiles, frowns, and other facial expressions to aid in creating an emotional profile.

Other physiological data can also be useful in determining the personal emotional profile of an individual. Gestures, eye movement, sweating, electrodermal (EDA) activity, heart rate, blood pressure, and respiration are a few examples of such potentially useful data sources. A variety of sensor types can be used to capture physiological data, including heart rate monitors, blood pressure monitors, EDA sensors, or other types of sensors. A camera can be useful for simultaneously capturing physiological data and facial images. Sensors coupled to a computer—in some embodiments, the same computer with which the user is interacting; in other embodiments, one or more other computers—can be configured to detect, capture, and/or measure one or more external manifestations of the user's emotional state. For example, a still camera can be configured to capture images of the user's face; a video camera can be configured to capture images of the user's movements; a heart rate monitor can be configured to measure the user's heart rate; a skin resistance sensor can be configured to detect changes in the user's galvanic skin response; and an accelerometer can be configured to measure such movements as gestures, foot tapping, or head tilts, to name a few. In embodiments, multiple sensors to capture the user's emotional state data are included.

Once the data has been collected from the individual, an analysis of the emotional state data is obtained, with the analysis providing insights on the emotional states of the user over time. In some cases, the emotional state of the user can be estimated. Software can be used to extract emotional state information from the physiological data captured in an image or video in order to augment, or replace, the data captured from a camera. In some embodiments, self-report methods of capturing emotional state information, such as the survey approach, are also used in conjunction with emotional state information captured from cameras, sensors, monitors, or other equipment.

Once the emotional state information has been produced, an output can be rendered to the individual. The output can be a quantitative textual personal emotional profile, a graphical representation for the individual, or some other representation. The output can include an analysis of other individuals whose cognitive state information has been correlated and compared to the profile of an individual. The emotional profile can include data and analysis that is posted on a social network web page. The profile can describe the well-being status of the individual. The profile can also describe recommendations for the individual. The recommendations can include activities such as watching a video, playing a game, or participating in a social activity. The emotional profile can also be used in concert with a calendar where it can be displayed or compared with ongoing activities already included a person's schedule. The process of generating and using an emotional profile can further comprise correlating a profile of an individual to a profile populated with previously established "norms." In embodiments, analysis includes aggregating the profile of the individual with the profiles of a plurality of other people, and correlating the profiles of a plurality of people with activities performed by this plurality. The correlated profiles of a plurality of people can be associated with a category useful in predicting future behaviors or responses.

FIG. 1 is a flow diagram for personal emotional profiling in a vehicle. A flow 100 that describes a computer-implemented method for personal emotional profiling is shown. The flow 100 includes obtaining cognitive state data on an individual 110. The obtaining can be accomplished by collecting cognitive state data using sensors, cameras, and other devices. The obtaining can be based on capturing facial images 112 of an individual within a vehicle as the individual responds to stimuli. The obtaining can be accomplished by accessing a database and importing cognitive state data from the database. In some embodiments, the cognitive state data is already present in a system as a result of previous accessing or data manipulation, and the obtaining simply comprises accessing the already present cognitive state data. The collecting of cognitive state data is accomplished using different methods in various embodiments, and can include capturing facial images of an individual as they respond to stimuli. Facial image data can be captured using any type of image-capture device including a webcam, a video camera, a still camera, a thermal imager, a CCD device, a phone camera, a three-dimensional camera, a depth camera, an infrared camera, multiple webcams used to show different views of a person, or any other type of image capture apparatus that allows captured data to be used in an electronic system. The general expressiveness and facial changes of an individual as they view input stimuli can be analyzed to determine an emotional state. A camera or another facial recognition device can be used to capture images of an individual's face, and software can be used to extract and interpret laughs, smiles, frowns, and other facial expressions. The obtaining of cognitive state data can be accomplished while a person observes various types of media including online media content. The obtaining can accomplished by collecting the cognitive state data over time. In embodiments, the obtaining is accomplished by collecting the cognitive state with a plurality of devices.

In some embodiments, the data is collected from multiple sources. The collected data can include any type of cognitive state data including, but not limited to, heart rate, respiration rate, blood pressure, skin resistance, audible sounds, gestures, or any other type of data that can prove useful for determining cognitive state information. In some embodiments, the cognitive state data includes electrodermal activity data. The cognitive state data for an individual can be obtained by analyzing a cognitive state in light of various other sources of information and generating a cognitive state, or personal emotional, profile based upon the cognitive state data.

The flow 100 can further comprise determining contextual information related to the collected cognitive state data. Any type of contextual information related to the collection of the cognitive state data can be obtained. Some examples of contextual information that can be collected include a task assigned to the user, the location of the user, the environmental conditions that the user is exposed to—such as temperature, humidity, and the like—, the name of the content being viewed, the level of noise experienced by the user, or any other type of contextual information. In some embodiments, the contextual information is based on one or more of skin temperature or accelerometer data. In some embodiments, the contextual information is based on one or more of a photograph, an email, a text message, a phone log, GPS information, or vehicle ambient conditions—both inside and outside the vehicle.

The flow 100 includes analyzing the cognitive state data 120 to produce cognitive state information. The analyzing of cognitive state data 120 can include various types of analysis, including computation of means, modes, standard deviations, or other statistical calculations over time. The analyzing of cognitive state data 120 can include inferring cognitive states. The cognitive state data can include one or more of smiles, laughter, smirks, or grimaces. The data sent can include image data, physiological data, and accelerometer data. The cognitive states which can be determined include happiness, sadness, concentration, and confusion, as well as many other cognitive states. The categorizing can be based on a plurality of expressions by the individual. The categorizing can further be based on a rate of change in the plurality of facial expressions by the individual. In embodiments, the rate of change is evaluated during exposure to specific media. Cognitive state data can be collected sporadically or continually over a time period to create a profile. The profile can include a summary of the cognitive state analysis. In some embodiments, the data which is sent to the server is a subset of the data that was captured on the individual. In some embodiments, a subset of the data collected on an individual is analyzed and sent to a server. The analyzing of the cognitive state data can be accomplished at least in part on a server, or server machine. The analyzing can be accomplished using a neural network and machine learning. The cognitive state data can pertain to an emotional state, a cognitive state, and/or a physiological state.

The flow 100 continues by sending cognitive state information to a server device 124. In some embodiments, the cognitive state information is generated in the form of a description or summary. The information can be sent to the server 124 for further mental profile analysis or for correlation with other people's profiles or analyses. In embodiments, the cognitive state data is analyzed by the computer with which the user is interacting, the computer or computers that captured the sensor data, and/or one or more other computers that can be local or remote to the user to produce the cognitive state information. In embodiments, the information sent to the server 124 remains in the form of cognitive state data. The data sent to the server can comprise various types of cognitive state data including, but not limited to, facial data, heart rate, respiration rate, blood pressure, skin resistance, skin temperature, accelerometer data, mental state inference, audible sounds, gestures, electrodermal data, and/or contextual data.

The cognitive state data 120 can be augmented with audio data 122. The audio data can be captured contemporaneously with video data to provide a more complete understanding of both the individual's environment and stimuli and the individual's cognitive state response to the stimuli. The cognitive state data 120 can augmented through emotional journaling 126. An individual might find that entering comments in a digital or online journal, using a journaling application, or writing their emotions down on paper can help them to process difficult times as well as to sort out general emotions. The information provided by the individual as part of their journaling may be included in the analysis used in developing a personal emotional profile.

The flow may comprise developing norms 128 for an individual. Emotional experiences, including contentedness, sadness, worry, joy, fury, fear, or regret, can result from a unique combination of thinking, behavior, and biophysiological changes which take place in the human body as it experiences a life event. In one sense, emotions can be conceptualized as dependent variables, with experiences serving as independent variables. Individuals who experience similar events can be categorized based on similar or dissimilar response to those events. Valence represents one variable that can aid in such categorization. Valence measures the intrinsic attractiveness (positive valence) or averseness (negative valence) of an event, object, or situation. Emotions with the similar valence (i.e. anger and fear) can result in a similar influence on judgments and choices among a plurality of individuals. Individuals can also exhibit similar emotional experiences based upon demographic criteria including age, education, race, location, and other factors. A variance from a person's expected responses to emotional stimuli can indicate a useful categorical difference that can be used to update an emotional profile. A personal emotional profile can include an analysis of a person's emotional state compared to certain norms. The flow 100 can include developing norms 128 for a plurality of individuals and these norms can be factored into emotional profiling. Activities and analysis can be used to develop norms applicable to a plurality of individuals. The norms established for a group can be based on a correlation of emotional responses from a plurality of individuals. The flow 100 can include the correlation of norms for an individual with the norms established for a group, including a demographic group.

The flow can include making recommendations 130 to the individual based on their personal emotional profile. This feedback can include recommendations for different activities, and can include recommendations for performing activities based upon time of day, a period of time during the day, or another type of calendar-based scheduling. The flow can further comprise using response differences of the individual, over an interval of time, from the norms for the individual to make a recommendation 130. For example, for an individual whose personal emotional profile correlates with the profiles of other individuals of a similar demographic category, a response to a particular event or circumstance for that individual that is different than the demographic norm can trigger the system to offer a different recommendation than the recommendation provided to the individuals scoring near the norm. The different response recommendations can become part of the individual's emotional profile. Response differences can be evaluated on an hourly, daily, weekly, monthly, or yearly basis. The recommendations can include activities such as watching a video, playing a game, or participating in a social activity, to name a few. The recommendations derived from the emotional profile can also be included in a calendar where they can be displayed or compared with the ongoing activities already included in the calendar. In some embodiments, an individual's emotional profile is correlated to emotions that occur in response to a particular activity. Additionally, the analysis can include aggregating the emotional profile of the individual with the emotional profile of a plurality of other people, and further correlating the emotional profile of a plurality of people with activities performed by the plurality in order to make a recommendation.

The flow can include developing norms for a demographic group 132. The characteristics of the group can include any demographic, such as age, sex, marital status, literacy/education, employment status and occupation, geographical location, place of birth, language, religion, nationality, ethnicity, race, and citizenship, among others. Individuals who comprise a group defined by one or more of these demographic attributes can potentially experience generally similar emotional responses to an event. In order to further refine the demographics-based classification, typical emotional response can be inferred based upon the aggregate response to an event or life circumstance from a plurality of members of the demographic group. The norm of the demographic, and any variances from the norm of the demographic, can be used to adjust or refine the emotional profile 134 of an individual or the emotional profile of a group. The flow 100 can include using response differences in the individual from the norms for the demographic group to refine a profile 134.

The flow 100 continues with correlating previously determined cognitive state information of the individual with the cognitive state information from a plurality of people 140. The correlation includes analysis that can identify complementary relationships based upon similar cognitive states resulting from similar events or life circumstances. The correlation between an individual and a group of individuals can be based upon data captured during an activity performed by the individual or the group of individuals. The activity can comprise an interaction with a web site, a movie, a movie trailer, a product, a computer game, a video game, a personal game console, a cell phone, a mobile device, an advertisement, or another action such as consuming food. As used herein, interaction refers to both passive viewing and active viewing and responding. The correlation between an individual and a group of individuals can be based upon data related to a demographic profile. Other characteristics of a plurality of individuals can be correlated with the characteristics of an individual to refine an emotional profile.

A media or service-type product can be categorized 144 based upon the emotional response of an individual or plurality of individuals. The categorizing can be part of an emotional profile. The similar response of a plurality of individuals to a media or service product can create a correlation among those individuals, which in turn can be categorized within a profile. The media/service product can include any type of content such as broadcast media, digital media, electronic media, multimedia, news media, print media, published media, recorded media, social media, online media, and other forms of media content. The emotional profile of an individual or plurality of individuals can be determined as the individual or plurality are watching or interacting with the media. Digital media can be categorized based on a profile. For example, some embodiments include a media presentation prepared with different versions, and, depending on the goal of the media presentation, collected emotional profile data can be used to determine which media presentation generated the most positive or negative affect data. Other embodiments use emotional profile information to determine the duration for the media presentation. In still other embodiments, the emotional profile information is used to determine the presentation location of a media presentation. In some embodiments, the media presentation is optimized for a specific platform, such as a mobile phone, tablet computer, or mobile device. Other embodiments optimize the media presentation for a home TV screen, a large movie theater screen, or a personal computer screen, based upon the analysis of an individual's emotional profile as they view various media on different devices. Likewise, the profile can be used to categorize, analyze, or optimize a product or service.

As emotional profile information is collected, the personal emotional profile of an individual is periodically updated 142. The profile can be updated in real time or can be updated at the conclusion of an event. The profile can be updated periodically, such as at a time of day, hourly, weekly, monthly, yearly, or using another calendar-based time frame. The profile can include a summary of an individual or plurality of individuals' cognitive state analysis. The updating can be based on data from an individual accumulated over time. The updating can be based on data from two or more vehicle journeys for the same individual. The vehicle journeys can be in the same vehicle or in two or more vehicles, such as in a fleet of vehicles from a ride-sharing service, a rental car service, a limousine service, a bus service, and so on.

The flow 100 includes categorizing the individual's cognitive state information against a personal emotional profile 150. A personal emotional profile can be categorically classified alongside other individuals' emotional profiles. The classification can comprise placing the individual's profile in a category to show a relationship between individuals based upon their emotional profile. The categorizing can include evaluation of facial expressions for anger, sadness, happiness, or disgust. The classification of individuals with related emotional profiles can be used to systematize and label an individual's emotional profile. For example, an individual's profile can be classified in an expressive category or a non-expressive category. Continuing, an individual's profile can be classified in a melancholy category or an anxious category along with profiles from other individuals exhibiting similar characteristic markers of anxiety or melancholy. Categories for classifying different emotional associations can be defined between complementary associations of emotional characteristics, such as sadness, contentedness, worry, excitement, calm, happiness, fear, anxiety, and others.

Categories can include expected responses to stimuli. For example, individuals could be categorized based on reactions to particular film types such as romantic films or action films. Categories and analysis can be included in charts, tables, and maps used to describe current, past, and/or future characteristics of a particular emotional profile. The categorization of emotional profiles can also be used to define types for both individuals and groups of individuals, including but not limited to demographic groups of individuals. A group's profile can be classified in a similar manner to an individual's profile, either by using emotional categories such as grouping by similar expressiveness measurements, or by using categories based on other criteria such as shared enjoyment of a particular movie genre. A profile indicating a generally fearful person could allow a vehicle to be manipulated in a certain way. For example, an autonomous vehicle with an individual occupant that has a personal emotional profile indicating a propensity to being fearful can provide vehicle manipulation instructions to slow the rate of acceleration upon detection that an individual's cognitive state information indicates concern, thus preventing a fully fearful reaction and the accompanying vehicle ride unpleasantness. Multiple occupants of a vehicle can be monitored to help control vehicle and/or driver action for a single vehicle or across a fleet of vehicles, such as those employed in a ridesharing service.

The flow 100 can include manipulating a vehicle 160, based on the cognitive state information, the categorizing, and the stimuli. Vehicle manipulation can use occupant image analysis. A camera within a vehicle can be used to collect cognitive state data including facial data, on an occupant of a vehicle. A cognitive state profile, or personal emotional profile, can be learned for the occupant. Once a personal emotional profile is learned, cognitive state data on the occupant can be captured while the occupant is in a second vehicle. It can be the same or a different vehicle from the learning vehicle. The further cognitive state data is compared with the cognitive state profile, and the second vehicle is manipulated based on the comparing of the further cognitive state data. The cognitive state profile, or personal emotional profile, can be communicated. The communicating of the cognitive state profile communication can include sending cognitive state profile information to one or more vehicles. The cognitive state profile communication can include manipulation of one or more vehicles. The manipulating can include commencing a locking out operation, recommending a break for the occupant, recommending a different route, recommending how far to drive, responding to traffic, adjusting seats, adjusting mirrors, adjusting climate control, adjusting lighting, adjusting music, adjusting audio stimuli, adjusting interior temperature, engaging brake activation, engaging steering control, and other vehicle control and manipulation techniques.

The personal emotional profiles can be sent to vehicles using a wireless link or other data transfer technique. The personal emotional profile that can be sent can be based on cognitive state data including facial data from a vehicle occupant. The cognitive state data including facial data can be collected using a camera or other image capture technique. The flow 100 can include collecting and augmenting the analyzed cognitive state data 120 with audio data 122 that can include voice data. The voice data can be collected from the occupant using a microphone or other audio capture technique. The voice data can include audio data, where the audio data can include traffic sounds, road noise, music, news, eBooks, etc. that can be played by the occupant, and so on. The voice data can be evaluated for timbre, prosody, vocal register, vocal resonance, pitch, loudness, speech rate, or language content. The voice data can also be used in evaluating the cognitive state or states of a vehicle occupant. The augmenting can be based on lexical analysis of the voice data that looks at sentiment.

The capturing facial images 112 and augmenting with audio data 122 can be based on collecting data from an interior of a vehicle. Vehicle manipulation can be based on using occupant image analysis. An occupant of a vehicle can be observed using a camera, a microphone, and other image and audio capture techniques. The image data can include video data. The video data and the audio data can include cognitive state data where the cognitive state data can include facial data. The occupant can be a driver of the vehicle, a passenger within the vehicle, and so on. The capturing facial images 112 and augmenting with audio data 122 can be based on collecting data from outside of a vehicle. Data captured from outside the vehicle can include traffic, weather, pedestrians, construction, and road conditions, to name just a few. The data captured outside the vehicle can be used to update the personal emotional profile. For example, if heavy traffic conditions outside of the vehicle and emotional distress inside the vehicle are recorded together in an individual's personal emotional profile, the profile can be sent to a fleet of vehicles, and then when the individual rides in another car from the fleet, the driver and/or autonomous or semiautonomous vehicle can plan a route that avoids heavy traffic. This type of vehicle manipulation based on an individual's personal emotional profile can engender customer satisfaction and repeat business, and it can create a more pleasant experience for the individual. In some embodiments, the personal emotional profile is transferred from vehicle to vehicle within a fleet, which can enable consistent experiences by an individual experiencing multiple vehicles from within the fleet.

The interior of a vehicle can be a standard vehicle, an autonomous vehicle, a semi-autonomous vehicle, and so on. The vehicle can be an automobile, a van, a sport utility vehicle (SUV), a truck, a bus, a special purpose vehicle, etc. The interior of the vehicle can include standard controls such as a steering wheel, a throttle control, a brake, and so on. The interior of the vehicle can include other controls such as controls for seats and mirrors, climate controls, etc. The controls of the vehicle can be controlled by a driver of the vehicle, an occupant of the vehicle, or a controller. The controller can control the vehicle in various manners such as autonomously, semi-autonomously, assertively to a vehicle occupant, etc. The controller can receive instructions via an antenna or by using other wireless techniques. The controller can be preprogrammed to cause the vehicle to follow a specific route.

The flow 100 can include making a recommendation for digital media based on the categorizing. The flow can include pushing media content to the individual based on the categorizing. The digital media can include one or more of a movie, a television show, a web series, a webisode, a video, a video clip, an electronic game, an e-book, an e-magazine, or another media presentation. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
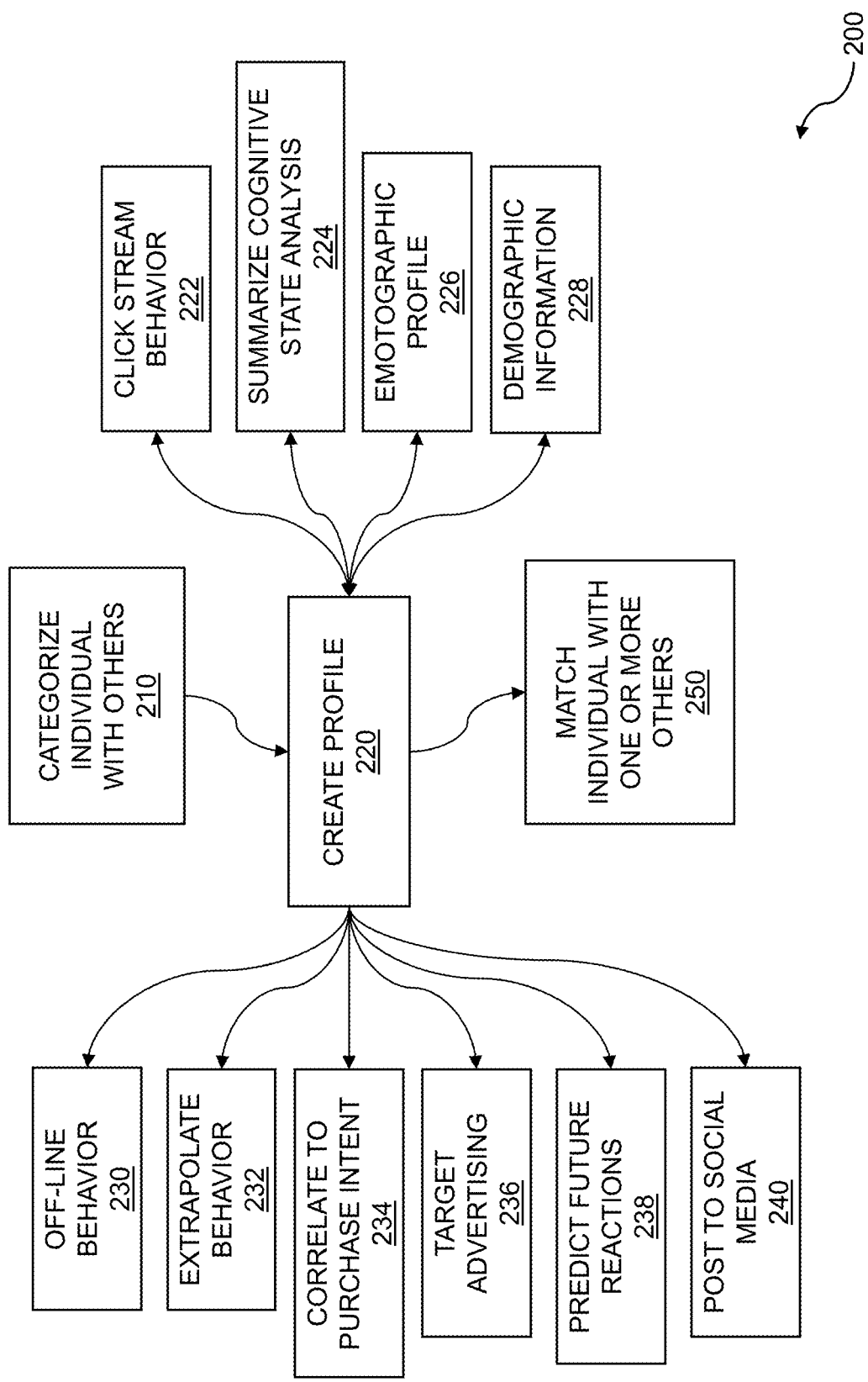
FIG. 2 is a flow diagram for personal emotional profile usage.

FIG. 2 is a flow diagram for personal emotional profile usage. The flow 200 can continue from or be part of the previous flow 100. The flow 200 can include having an individual's emotional profile placed in a category along with other individuals' emotional profiles 210. The categorizing can comprise matching the individual with one or more people from a plurality of people, based upon how both the individual and the one or more other people are categorized. The categorization can also be used to define types for both individuals and groups of individuals, including but not limited to demographic groups of individuals as set out in the description for FIG. 1. The categorization of an individual or a group of individuals can be used to create an individual's personal emotional profile 220.

The personal emotional profile of an individual can comprise a clickstream behavior 222. A clickstream is a recording of the parts of the screen a computer user clicks on while web browsing or using another software application. As the user clicks anywhere in the webpage or application, the action is logged. The clickstream behavior 222 of an individual or plurality of individuals can be used to group the individual or the plurality of individuals into a category. The profile of an individual can further be correlated with the profiles of a plurality of individuals to predict clickstream behavior for the individual. The analysis can be used to modify a web page or application based on the emotional profile created by using clickstream data.

Personal emotional profile information can also be used to create a summary based upon an analysis of an individual's cognitive state 224. A summary can include a user's personal emotional state, a category for an emotional profile, demographic and other statistical information, and other criteria such as perceptions, sensations, dreams and daydreams, moments of despair, boredom, flashes of inspiration, recollections, images seen in the mind's eye, thoughts, and many others. This summary can be compared to and correlated with the summary emotional profile information from other individuals in order to include the individual in a previously defined category.

The personal emotional profile can comprise an emotographic profile 226. The emotographic profile can include emotional data, statistics, and categories of emotions that can be used to characterize, label, or type an individual or plurality of individuals. The emotographic profile of an individual can include information about the individual's adherence to, or deviation from, the norms of a plurality of individuals. The emotographic profile of an individual can include a category of similarly situated individuals. The profile can also include demographic information 228. Additionally, personal emotional profile information can also be used to further define or augment demographic information 228 of an individual or plurality of individuals. The demographic characteristics used to classify the individual and/or the group can include any demographic including but not limited to age, sex, marital status, literacy/education, employment status and occupation, geographical location, place of birth, language, religion, nationality, ethnicity, race, and citizenship. In some embodiments individuals who comprise a group defined by one or more demographic attributes such as those listed above will experience generally similar emotional responses to an event. A normal emotional response to a given event can be inferred based upon the aggregate response to an event or life circumstance from a plurality of members of the certain demographic group. In embodiments, demographic information is combined with emotographic profile information to categorize, label, or type an individual or plurality of individuals.

The flow 200 can include off-line behavior 230 of an individual or plurality of individuals. In embodiments, off-line behavior demonstrated by an individual is inspected by comparing the individual's off-line behavior to the off-line behavior of a plurality of individual previously analyzed to determine norms for off-line behavior. The behaviors can be correlated to form a category. An individual can be categorized based upon their adherence to, or deviation from, the expected responses for a given category. The flow 200 can further comprise extrapolating behavior 232. The future behavior of an individual can be predicted based upon the correlation of the individual to other individuals in a similar circumstance. For example, individuals whose emotional profile has been categorized as including melancholic tendencies could be predicted to enjoy long solitary walks, as a preference for long solitary walks has been extracted as a behavioral norm as among a group of individuals whose profiles include melancholic tendencies. Similarly, individuals whose emotional profile has been categorized as including delight could be predisposed to purchasing flowers. Therefore, the use of emotional profile generation can have important advantages to those interested in, for example, understanding the types of people who visit a company's website, and can aid in the correlation of an individual's intent to make a purchase 234. The flow 200 can further comprise correlating a component of the emotional profile to a purchase intent 234. Certain emotional profiles can represent individuals predisposed to impulse purchases while other emotional profiles can correspond to individuals who purchase based on extensive research. Certain emotional profiles can be correlated to individuals with a greater affinity to the purchase of certain products or services.

The flow 200 can include targeting advertisements 236 based on the profile. Emotional profile generation can give advantages to those interested in assessing the effectiveness of advertising, and, in embodiments, can help advertisers appropriately target advertising 236 to an individual or plurality of individuals. An advertisement can be shown to an individual because the individual previously evidenced a positive emotional profile state in response to certain similar advertisements. In some embodiments, an advertisement that correlates to the emotional profile of an individual based upon a period of time, time of day, or another calendar time frame is shown to an individual. Advertisement timing can be chosen based upon the emotional profile status of an individual. For example, by selecting the correct time point for an advertisement to be shown based upon the profile status of an individual, viewers can be retained through commercial breaks in a program. Various types of cognitive state information, such as excitement, interest, or other emotional profile information can be used to automatically determine advertisement placement. In other embodiments, the advertisements are offered in different locations, with emotional profile data collected in order to determine which advertisement placement generates the most desirable emotional status. The response to an advertisement by an individual can be correlated with the response to the advertisement by a plurality of people to categorize the profiles of the group. The profile of an individual can be refined based upon their adherence to, or deviation from, the norms established for the category.

Thus, emotional profile generation could aid business marketers, among others, in predicting an individual's willingness to make a purchase or might infer a predicted response to an advertisement. Personal emotional profiles can also be used to predict future reactions 238 to many other events or life circumstances including prediction of future reactions 238 to stimuli. Emotional profiles can be used to improve the accuracy of emotional forecasts for events or life circumstances. Also, emotional profiles generated to include demographic, emotographic, or other group associations can be used to predict the future reactions of a group to similar events or similar life circumstances. The response to an event or life circumstance by an individual can be correlated with the response to the event or life circumstance by a plurality of people to categorize the profiles of the group. The profile of an individual can be refined based upon their adherence to, or deviation from, the norms established for the category. The flow 200 can include using the profile to predict a preference.

The flow 200 can include posting a representation of the profile to a social media site 240. In various embodiments, the rendering can be graphical, pictorial, textual, auditory, or any combination thereof. In some embodiments, the emotional profile is represented by an avatar. The avatar can be selected by the individual. The avatar can be animated based on the emotional profile information. For example, if the individual is excited, the avatar may change to an appearance suggesting excitation.

The flow 200 can include matching the individual emotional profile with one or more profiles from a plurality of other people 250, based on the categorizing. For example, the emotional profile could be used to match entrepreneurs with different but compatible skills in technology startups, or match potentially compatible couples on dating websites. By matching the emotional responses of individuals with the emotions of a plurality of individuals, norms for a group, including a demographic group, can be analyzed. By analyzing the response differences of an individual from the norms established for the group, an individual profile can be refined. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
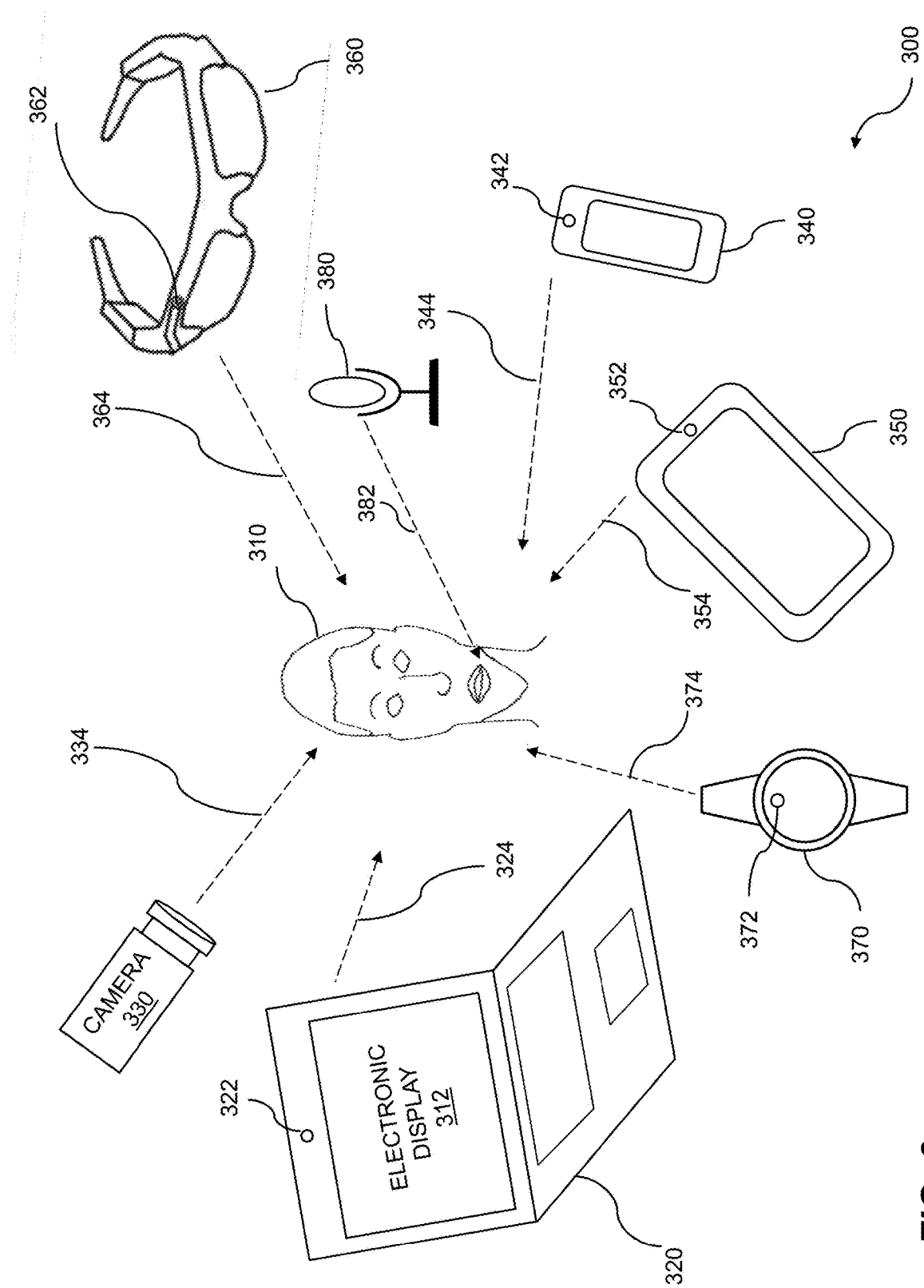
FIG. 3 shows example image and audio collection including multiple mobile devices.

FIG. 3 shows example image and audio collection including multiple mobile devices. Cognitive state data including image data, audio data, and physiological data, can be collected using multiple mobile devices. The collected cognitive state data can be analyzed and be used for personal emotional profile generation for vehicle manipulation. Cognitive state data is obtained from an individual, where the cognitive state data is extracted, using one or more processors, from facial images captured of an individual as they respond to stimuli within a vehicle. The cognitive state data extracted from facial images is analyzed to produce cognitive state information. The cognitive state information of the individual is correlated with cognitive state information from a plurality of people. The cognitive state information is augmented based on audio data collected from within the vehicle contemporaneously with the facial images. One or more processors are used to categorize the individual with others from the plurality of people based on the correlating and the augmenting. The vehicle is manipulated based on both the cognitive state information that was augmented and the categorizing.

While one person is shown, in practice the video data or audio data on any number of people can be collected. In the diagram 300, the multiple mobile devices can be used separately or in combination to collect video data, audio data, physiological data, or some or all of video data, audio data, and physiological data, on a user 310. While one person is shown, the video data, audio data, or physiological data can be collected on multiple people. A user 310 can be observed as she or he is performing a task, experiencing an event, viewing a media presentation, and so on. The user 310 can be shown one or more media presentations, political presentations, social media, or another form of displayed media. The one or more media presentations can be shown to a plurality of people. The media presentations can be displayed on an electronic display 312 or another display. The data collected on the user 310 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 310 can be analyzed and viewed for a variety of purposes including expression analysis, cognitive state analysis, mental state analysis, emotional state analysis, and so on. The electronic display 312 can be on a laptop computer 320 as shown, a tablet computer 350, a cell phone 340, a television, a mobile monitor, or any other type of electronic device. In one embodiment, video data including expression data is collected on a mobile device such as a cell phone 340, a tablet computer 350, a laptop computer 320, or a watch 370. Similarly, the audio data including speech data and non-speech vocalizations can be collected on one or more of the mobile devices. Thus, the multiple sources can include at least one mobile device, such as a phone 340 or a tablet 350, or a wearable device such as a watch 370 or glasses 360. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 322, a phone camera 342, a tablet camera 352, a wearable camera 362, and a mobile camera 330. A wearable camera can comprise various camera devices, such as a watch camera 372. Sources of audio data 382 can include a microphone 380.

As the user 310 is monitored, the user might move due to the nature of the task, boredom, discomfort, distractions, or for another reason. As the user moves, the camera with a view of the user's face can be changed. Thus, as an example, if the user is looking in a first direction, the line of sight 324 from the webcam 322 is able to observe the user's face, but if the user is looking in a second direction, the line of sight 334 from the mobile camera 330 is able to observe the user's face. Furthermore, in other embodiments, if the user is looking in a third direction, the line of sight 344 from the phone camera 342 is able to observe the user's face, and if the user is looking in a fourth direction, the line of sight 354 from the tablet camera 352 is able to observe the user's face. If the user is looking in a fifth direction, the line of sight 364 from the wearable camera 362, which can be a device such as the glasses 360 shown and can be worn by another user or an observer, is able to observe the user's face. If the user is looking in a sixth direction, the line of sight 374 from the wearable watch-type device 370, with a camera 372 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 310 can also use a wearable device including a camera for gathering contextual information and/or collecting expression data on other users. Because the user 310 can move her or his head, the facial data can be collected intermittently when she or he is looking in a direction of a camera. In some cases, multiple people can be included in the view from one or more cameras, and some embodiments include filtering out faces of one or more other people to determine whether the user 310 is looking toward a camera. All or some of the expression data can be continuously or sporadically available from the various devices and other devices.

The captured video data can include facial expressions and can be analyzed on a computing device such as the video capture device or another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 4:
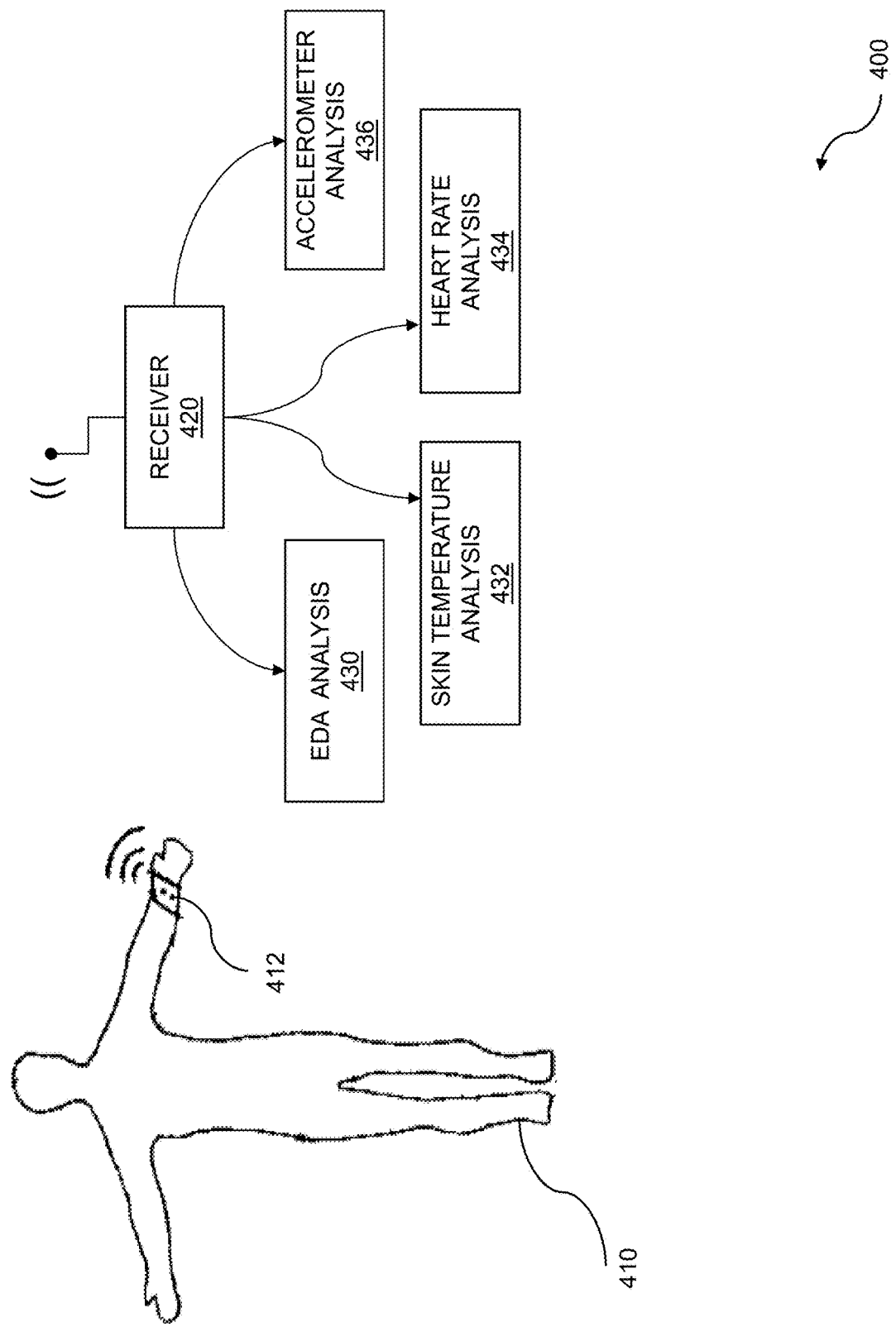
FIG. 4 illustrates a biosensor on a person.

FIG. 4 illustrates a biosensor on a person. The biosensor information can be used in the generation of an emotional profile. A diagram 400 shows various techniques a biosensor could use to provide the data needed to create the personal emotional profile of an individual. Physiological data can be gathered from a person 410 to determine their emotional state. A physiological monitoring device 412 can be attached to a person 410. The monitoring device 412 can be used to capture a variety of types of physiological data from a person 410 as the person experiences and interacts with various stimuli. The physiological data can include one or more of heart rate, heart rate variability, blink rate, electrodermal activity, skin temperature, respiration, accelerometer data, and the like. The physiological data can be derived from a biosensor. In embodiments, a plurality of people can be monitored as they view and interact with various stimuli.

A person 410 can experience and interact with various stimuli in a variety of ways. Physiological data collected from a person 410 as he or she interacts with various stimuli can be transmitted wirelessly to a receiver 420. In embodiments, physiological data from a plurality of people is transmitted to a receiver 420 or to a plurality of receivers. Wireless transmission can be accomplished by a variety of techniques including, but not limited to, IR, Wi-Fi, Bluetooth, and the like. In embodiments, the physiological data can be sent from a person to a receiver via tethered or wired methods. Various types of analysis can be performed on the physiological data gathered from a person or a plurality of people in order to determine their emotional profile. For example, electrodermal activity (EDA) 430 data can be analyzed to identify specific characteristics of an individual's emotional state. The electrodermal activity data can also be analyzed to determine a specific activity's peak duration, peak magnitude, onset rate, decay rate, and the like.

Additional types of analysis can be performed on the physiological data gathered from a person or a plurality of people to determine the people's collective or individual emotional profiles. For example, skin-temperature analysis 432 can be performed to measure skin temperature, temperature change rate, temperature trending, and the like. Heart rate analysis 434 can also be performed. Heart rate analysis can include determining heart rate, changes in heart rate, and the like. Further analysis of physiological data can include accelerometer analysis 436. Accelerometer data analysis can include determining activity, rate of activity, and the like. In embodiments, other types of analysis are performed on physiological data gathered from a person or a plurality of people to determine the emotional profile of an individual or a plurality of individuals.

Figure 5:
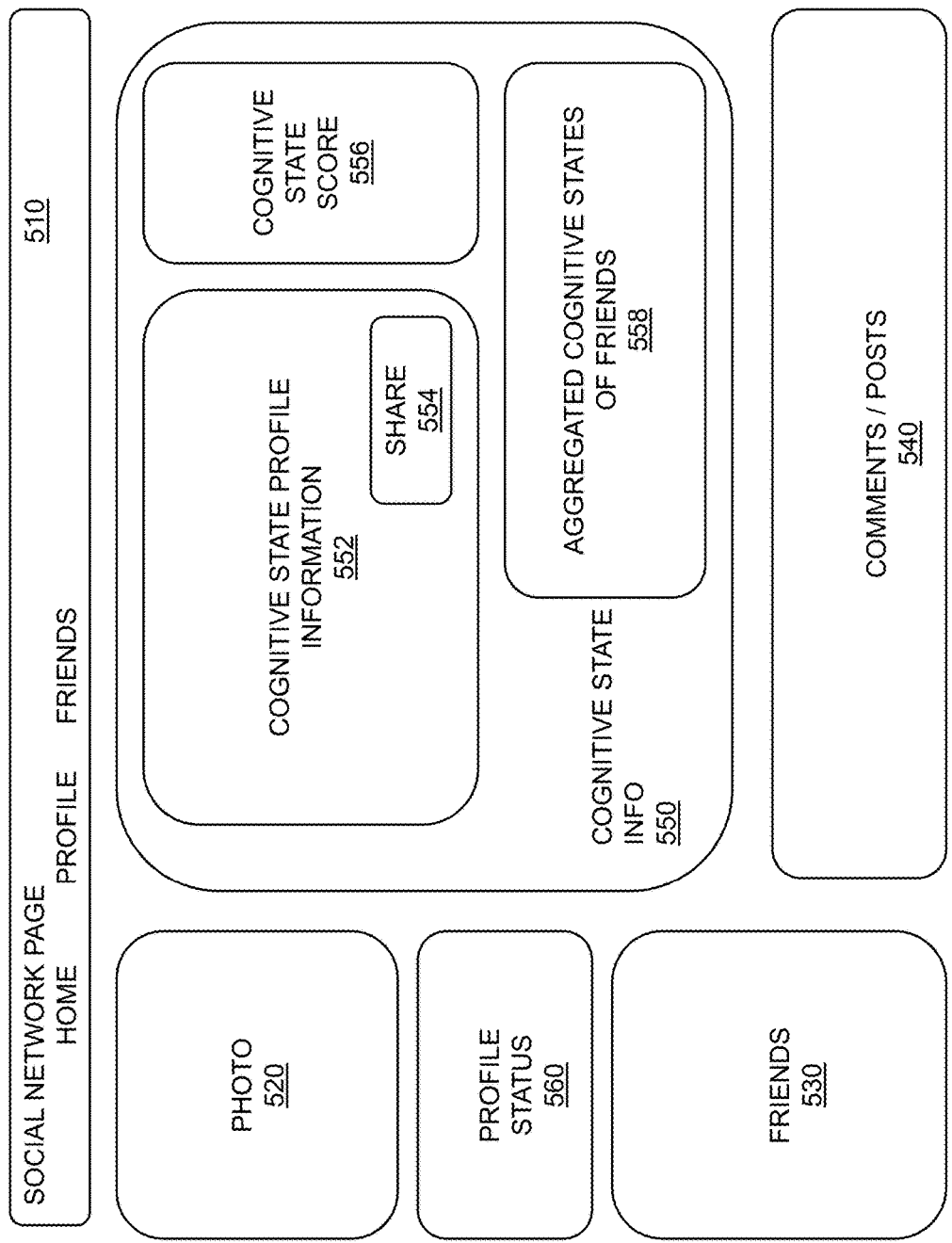
FIG. 5 shows a social network page with profile information.

FIG. 5 shows a social network page with profile information, where the profile information is related to emotional profiles. Emotional profile information can be generated based on cognitive state analysis. The emotional profile generation can include personal emotional profile generation for vehicle manipulation. The example page can include posting a representation of the profile to a social media site. The exact content and formatting can differ among various social networks. Similar content can be formatted for a variety of social networks including, but not limited to, blogging websites, Facebook™, LinkedIn™, Tumblr™, Twitter™, Instagram™, or other social networks. A social network page for a particular social network can include one or more of the components shown in the example social network page content 500, but can also include various other components in place of, or in addition to, the components shown. The social network content 500 as shown in the example can include a header 510 to identify the social network and can include various tabs or buttons for navigating the social network site, such as the "Home," "Profile," and "Friends" tabs shown. The social network content 500 can also include a profile photo 520 showing the individual that owns the social network content 500. Various embodiments also include a friends list 530 showing the contacts of the individual on the particular social network. Some embodiments include a comments/posts component 540 to show posts and various comments from the individual, friends, or other parties.

The social network content 500 can include the emotional profile status of the individual 560. In various embodiments, the rendering can be graphical, pictorial, textual, auditory, or any combination thereof. In some embodiments, an avatar can be used to communicate emotional profile information.

The social network content 500 can include a cognitive state information section 550. The cognitive state information section 550 can allow for posting cognitive state information to a social network page. The posted cognitive state information can include cognitive state information that has been shared by the individual or can include cognitive state information that has been captured but not yet shared, depending on the embodiment. In at least one embodiment, a cognitive state graph is displayed to the individual showing the individual's own cognitive state information 552 while viewing a web-enabled application. If this cognitive state information has not yet been shared over the social network, a share button 554 can be included. If the individual clicks on the share button 554, cognitive state profile information 552, such as a cognitive state graph or emoticon, or various summaries of the cognitive state information, can be shared over the social network. The cognitive state information can be shared with another individual, a group or subgroup of contacts or friends, another group defined by the social network, or openly with anyone, depending on the embodiment and the individual's selection. The profile photo 520, or another image shown on the social network, can be updated with an image of the individual demonstrating in some manner the cognitive state information that is being shared, such as a smiling picture if the cognitive state information indicates happiness. In some cases, the image of the individual is taken during a peak time of cognitive state activity. In some embodiments, the photo 520 section or some other section of the social network page 500 allows for posting video of the individual's reaction or representing the individual's cognitive state information along with the photo. If the cognitive state information shared is related to a web-enabled application, forwarding a reference to the web-enabled application as a part of the sharing of the cognitive state information can be performed and can include a URL and a timestamp indicating a specific point in a video. Other embodiments include an image of material from the web-enabled application or a video of material from the web-enabled application. The forwarding, or sharing, of the various cognitive state information and related items can be accomplished on a single social network, or some items can be forwarded on one social network while other items are forwarded on another social network. In some embodiments, the sharing is part of a rating system for the web-enabled application, such as aggregating cognitive state information from a plurality of users to automatically generate a rating for videos.

Some embodiments include a cognitive state score 556. In some embodiments, the cognitive state data is collected over a period of time and the cognitive state information that is shared reflects a mood for the individual and is displayed in the form of a cognitive state score 556. The cognitive state score can be a number, a sliding scale, a colored scale, various icons or images representing moods, or any other type of representation. Various moods can be represented, including, but not limited to, frustration, confusion, disappointment, hesitation, cognitive overload, focusing, being engaged, attending, boredom, exploration, confidence, trust, delight, and satisfaction. Some embodiments include a section for aggregated cognitive states of friends 558. This section can include an aggregated mood of those friends shown in the friends section 530 who have opted to share their cognitive state information. In some embodiments, the social network page can have an interface for querying well-being statuses across the social network. The query can be directed towards people to whom an individual is linked, to friends, to a demographic group, or to some other grouping of people. Embodiments can include aggregated cognitive states of those friends who have viewed the same web-enabled application as the individual, thus allowing the individual to compare their cognitive state information in the cognitive state profile information 552 to their friends' aggregated cognitive state information 558. Other embodiments display various aggregations from different groups.

Figure 6:
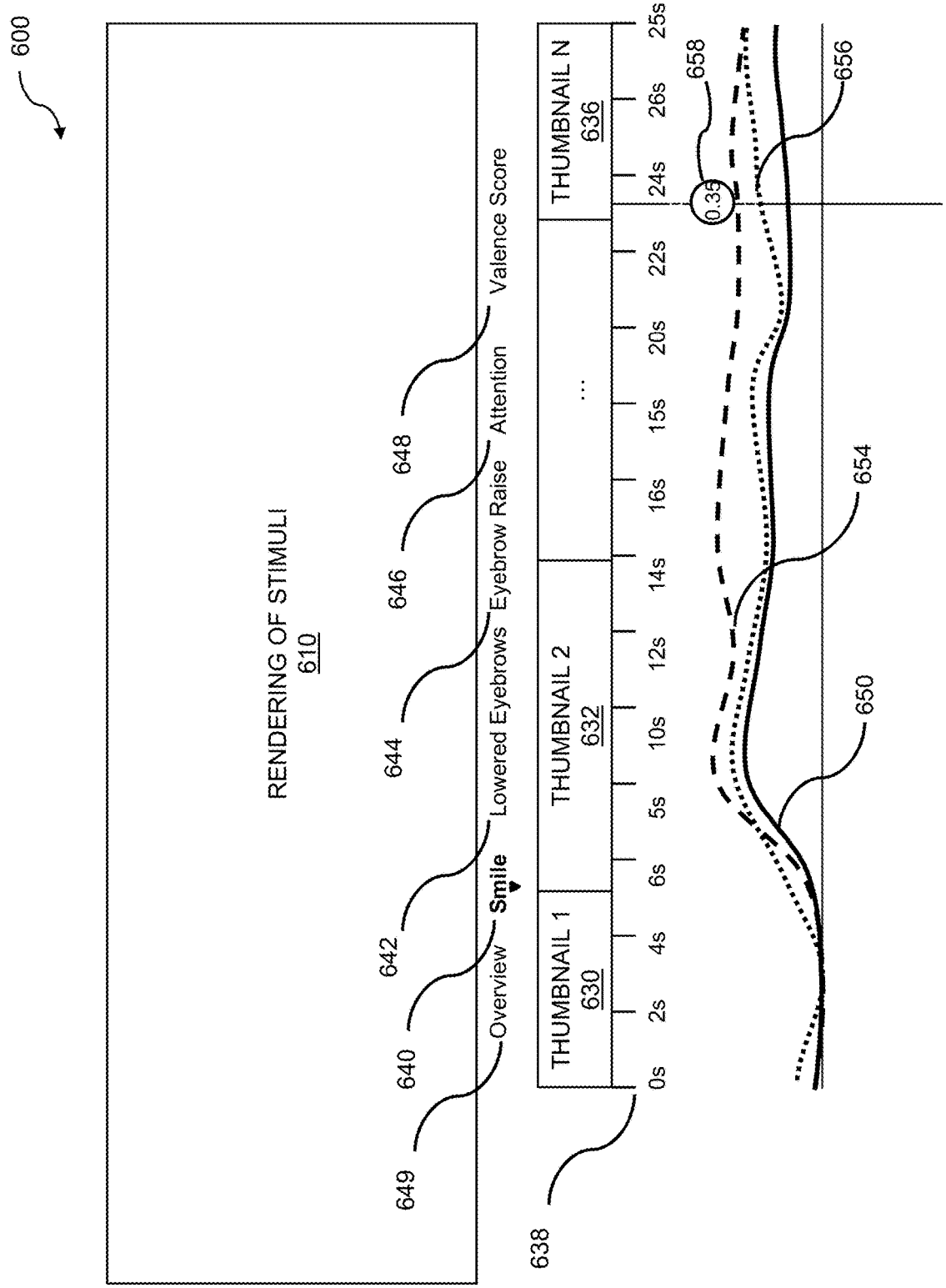
FIG. 6 illustrates rendering of personal emotional analysis.

FIG. 6 illustrates rendering of personal emotional analysis. Such rendered analysis can be useful for generating an emotional profile or for displaying the results of an emotional profiling effort. The emotional profile, such as a personal emotional profile, can be generated based on cognitive state analysis. Personal emotional profile generation can enable vehicle manipulation. The rendering 600 can be shown on any type of display including, but not limited to, a television monitor, a projector, a computer monitor (including a laptop screen, a tablet screen, a netbook screen, and the like), a cell phone display, a mobile device, or another electronic display. A rendering of stimuli 610 can be presented in the display. The example rendering 600 shown includes the rendered stimuli 610 along with associated cognitive state information. In some embodiments, a user can select among a plurality of stimuli. A list box or drop-down menu can be used to present a list of various stimuli for display. The user interface can allow a plurality of parameters to be displayed as a function of time, synchronized to the stimuli. Various embodiments can have any number of selections available for the user, with some being other types of renderings instead of video, including audio, text, still images, or other kinds of media. A set of thumbnail images for the selected rendering—in the example shown, the thumbnails include Thumbnail 1 630 and Thumbnail 2 632 through Thumbnail N 636—can be shown below the rendering along with a timeline 638. The thumbnails can show a graphic "storyboard" of the stimuli rendering 610. In some embodiments, one or more of the thumbnails are vignettes that include motion. The storyboard can assist a user in identifying a particular scene or location within the media presentation 610. Some embodiments do not include thumbnails, or have a single thumbnail associated with the stimuli presentation 610. Other embodiments have thumbnails of equal length while still others have thumbnails of differing lengths. In some embodiments, the start and/or end of the thumbnails is determined based on changes in the captured viewer cognitive states associated with the rendering, or is based on particular points of interest in the stimuli presentation 610. Thumbnails showing the one or more viewers can be shown in addition to, or in place of, the media-presentation thumbnails, such as thumbnail 1 630 and thumbnail 2 632 through thumbnail N 636, along the timeline 638. The thumbnails showing viewers can include peak expressions, expressions at key points in the stimuli, and the like.

Some embodiments include the ability for a user to select a particular type of cognitive state information for display using various buttons or other selection methods. For example, in the rendering 600 shown, the user has previously selected the Smile button 640, because smile cognitive state information is displayed. Other types of cognitive state information available for user selection in various embodiments include the Lowered Eyebrows button 642, Eyebrow Raise button 644, Attention button 646, Valence Score button 648, or other types of cognitive state information, depending on the embodiment. In embodiments, an Overview button 649, which allows a user to display graphs of the multiple types of available cognitive state information simultaneously, is available. The rendering 600 may include inferred cognitive states about the stimulus based on the cognitive state data which was collected. The cognitive states can include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The cognitive state information can include probability information for one or more effectiveness descriptors and the probabilities for the one of the one or more effectiveness descriptors can vary for portions of the advertisement.

Because the Smile option 640 has been selected in the example shown, smile graphs are displayed. In this example, a male smile graph 650 and a female smile graph 654 are shown, with the aggregated cognitive state information displayed visually. Another collective graph 656 for smiles by a different subset of people can be shown as well. The cognitive state information can be based on various demographic groups as they react to given stimuli. The various demographic-based graphs can be visually differentiated using various line types as shown in FIG. 6, or can be indicated using color or another method of differentiation. In embodiments, a slider is included to allow a user to select a particular time on the timeline and shows the value of the chosen cognitive state for that particular time. The slider can be rendered using the same line type or color as the demographic group whose cognitive state information is under analysis. A value 658 can be included with the slider to indicate a numeric representation of a specific value for the cognitive state of a chosen demographic at a particular time, or the value can be included to numerically display another useful measurement.

A user might be interested in evaluating the cognitive state of a particular demographic group, such as people of a certain age range or gender. In some embodiments, the cognitive state data is compared with self-report data collected from a group of viewers. In this way, the analyzed cognitive states can be compared with the self-report information to see how well the two data sets correlate. The rendered analysis 600 can be used to optimize the emotional profile. In some cases, different versions of the stimuli are available by using selection buttons. Further, there can be additional buttons for selection which allow for different types of optimization of the stimuli presentation.

Figure 7:
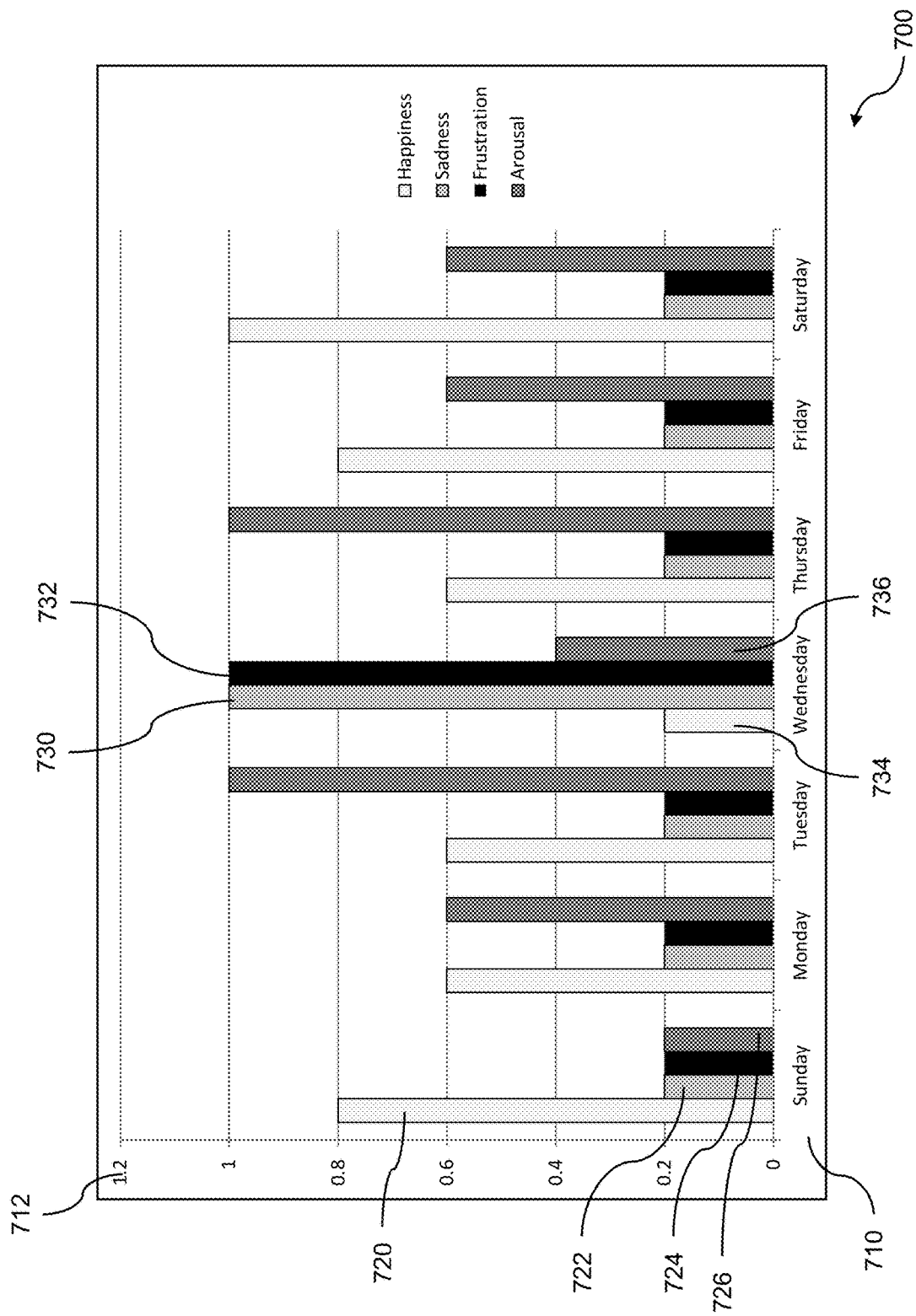
FIG. 7 shows a bar graph with cognitive states.

FIG. 7 shows a bar graph with cognitive states. The bar graph can include cognitive states across a period time. Graphing cognitive states using a bar graph or other technique can aid in visualizing an emotional profile such as a personal emotional profile, aspects of an emotional profile, the results of an emotional profiling effort, and so on. The graph 700 can be presented on any type of a display appropriate to displaying such data, including, but not limited to, a television monitor, a projector, a computer monitor (including a laptop screen, a tablet screen, a net book screen, and the like), a cell phone display, a mobile device, or another electronic display, or the graph can be printed. The graph can include one or more cognitive state parameters based on cognitive state information. The example graph 700 shows a weekly calendar 710 from Sunday through Saturday, but displaying across any period of time, including a day, a month, a year, or another period could be useful. In the example graph 700, cognitive state parameters are shown including happiness (720 and 734), sadness (722 and 730), frustration (724 and 732), and arousal (726 and 736). Any number of cognitive state parameters appropriate to cognitive state analysis can be graphed. The graph can be generated to show one or more cognitive state parameters for a specific time period. Similarly, the graph can display a scale 712 appropriate to the various parameters, such as a range of values between zero and one. Any units, scale, or range of values appropriate to the given parameters can be graphed.

The cognitive state parameters in a graph can be analyzed for various purposes including identification of trends, consistency, abrupt changes, and so on. The amount of cognitive state parameter value change that signals an abrupt change can be chosen from a value, range of values, and so on. Graph 700 illustrates some abrupt changes in the example parameters for the day Wednesday. While graphed information in the example shows relative consistency in the values of the various parameters along with some positive or negative trends for the week, the example cognitive state parameter values for Wednesday are markedly different. In the example shown, the parameter happiness 720 has a value of 0.8 on Sunday but only a happiness value 734 of 0.2 on Wednesday. In addition, sadness 722 and frustration 724 both have a value of 0.2 on Sunday, but change abruptly on Wednesday to values of 1.0 for sadness 730 and 1.0 for frustration 732. Finally, the parameter arousal 726 has a value of 0.2 on Sunday and an arousal value 736 of 0.4 on Wednesday. Identification of abrupt changes in the various cognitive state parameters which are presented in a graph can be useful for a variety of purposes including studying an individual, a plurality of individuals, a demographic group such as people of a certain age range or gender, and so on. In some cases, an emotional profile is generated for an individual or group of people where a trend for cognitive states can be anticipated through the week. After predicting the trend, the profile could be used to suggest activities. Deviations from the profile, such as an elevation in sadness and frustration, could be used to alter recommendations. In some cases, the recommendations could include exercising, watching a movie, visiting a counselor, or other activities.

The cognitive state parameters in a graph can be dependent on or independent of each other. For example, happiness 720 can inversely depend on or inversely track with sadness 722. Similarly, happiness might not be dependent upon nor track with another parameter. For example, happiness 720 might not depend on nor track with arousal. The graph can be analyzed to identify interdependencies between and among various cognitive state parameters or other parameters. For example, an increase in one parameter may correlate with a rise or a fall in another parameter.

Figure 8:
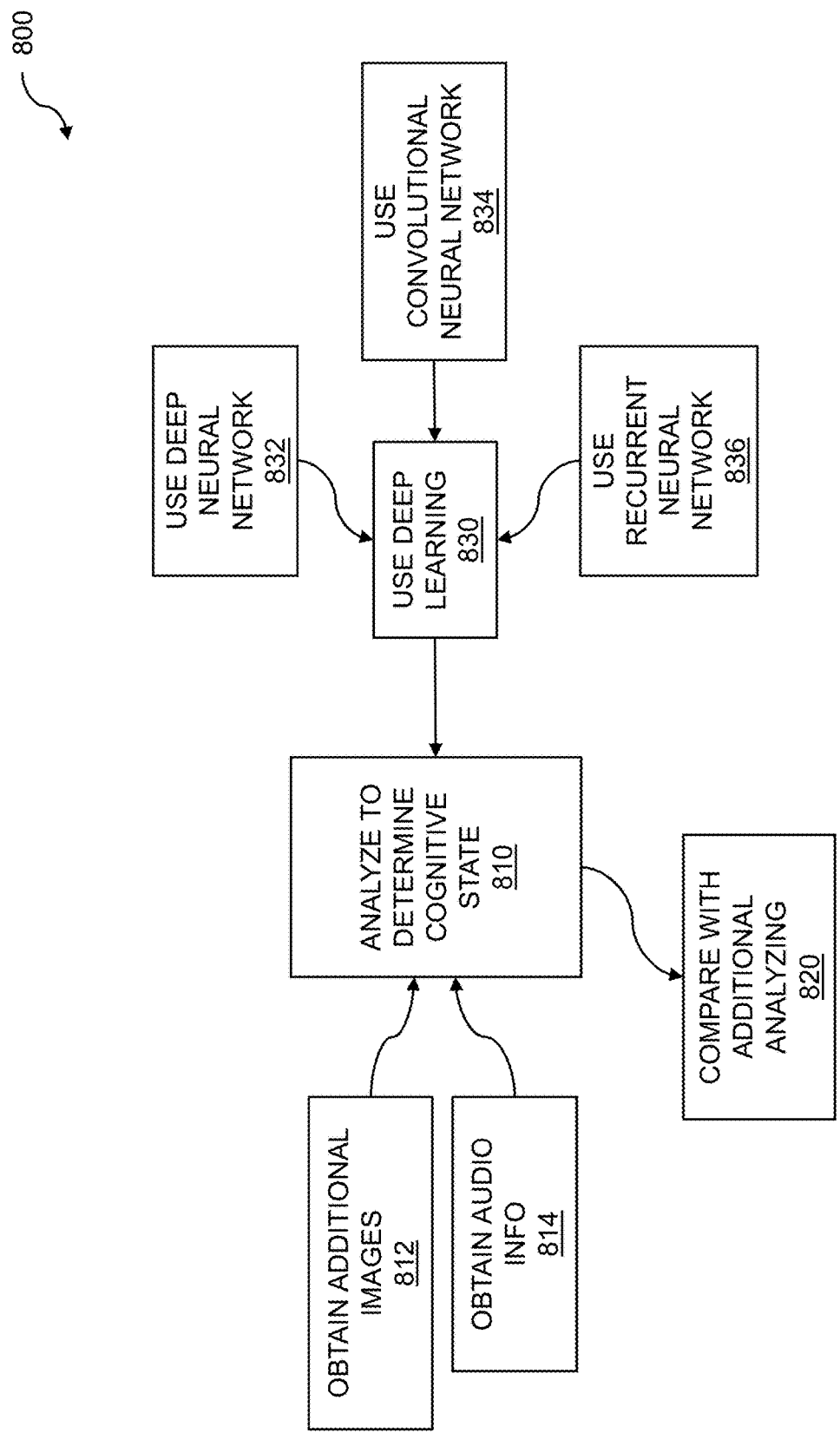
FIG. 8 is a flow diagram for further cognitive state analysis.

FIG. 8 is a flow diagram for further cognitive state analysis. Additional cognitive state data such as images, audio information, physiological information, and so on, can be obtained and analyzed to determine a cognitive state. The further cognitive state analysis supports personal emotional profile generation for vehicle manipulation. The cognitive state information of an individual can be correlated with cognitive state information from a plurality of other people. The additional cognitive state information can augment previously obtained cognitive state information. The individual can be categorized with the other people, and the vehicle can be manipulated based on the augmented and categorized cognitive state information. The flow 800 includes analyzing, using a computing device, additional cognitive state data to determine a cognitive state 810. The computing device can include an on-vehicle computing device, an electronic device such as a smartphone or table computer associated with the vehicle occupant, and so on. The computing device can include a computing device located beyond the vehicle, where the computing device can include a computing device in another vehicle, a server, a blade server, a cloud server, a mesh server, and the like.

The flow 800 includes obtaining additional images 812 of one or more additional occupants of the vehicle, where the additional images are analyzed to determine one or more additional cognitive states 810. Images of the one or more additional occupants of the vehicle can be obtained using imaging devices within a vehicle. The images can include visible light images, near-infrared images, or images comprising other spectra, where the images of any type include facial data. The flow 800 includes obtaining audio information 814 from the occupant of the vehicle and augmenting the analyzing based on the audio information. The audio information can be obtained using a microphone, audio transducer, etc., where the microphone, for example, can be an in-vehicle microphone, a microphone coupled to an electronic device associated with a vehicle occupant, etc. The microphone can obtain a variety of audio information such as in-vehicle sounds, exterior sounds such as road noise, wind noise, or traffic noise, etc. In embodiments, the audio information can include speech. The speech information can include speech from the occupant of the vehicle, speech detected in an audio source such as a radio or streaming station, and the like. In other embodiments, the audio information can include non-speech vocalizations. The non-speech vocalizations can include a variety of human generated sounds. In embodiments, the non-speech vocalizations can include grunts, yelps, squeals, snoring, sighs, laughter, filled pauses, unfilled pauses, or yawns. Additional information such as physiological information from the occupant of the vehicle can be obtained. The flow 800 includes comparing the cognitive state with additional analyzing 820, based on the physiological information or other related information that was obtained. The physiological information can be inferred from image data or audio data, collected using sensors, and so on. The physiological information can include heart rate, heart rate variability, respiration rate, skin conductivity, and the like.

The flow 800 includes analyzing, where the analyzing is performed using deep learning 830. Deep learning can be based on learning one or more representations related to data, rather than relying on algorithms that can be specific to a given data analysis task. Data representations, such as those based on feature learning, include techniques for automating the discovery, by a deep learning system, of representations that can be used to classify or detect features in raw data. In embodiments, the learning is performed using a deep neural network 832. A deep neural network can include an input layer, an output layer, and hidden layers internal to the neural network. A deep learning network can use weights, biases, and layers that can be learned as part of training the deep neural network. A deep neural network can include a feed-forward network, in which data such as training data or raw data can flow from an input layer, through the neural network, to an output layer. In other embodiments, the learning is performed using a convolutional neural network (CNN) 834. A convolutional neural network can include properties such as space invariance, shift invariance, or translation invariance, which are particularly useful properties for image analysis. A CNN can require little preprocessing of input data because the CNN can learn filters. The learning the filters can obviate the need to code the filters. The filters can enhance image classification tasks such as facial data analysis. In further embodiments, the learning is performed using a recurrent neural network 836. A recurrent neural network (RNN) can include connections between nodes to form a directed graph. The directed graph can be along a sequence. An RNN can exhibit temporal behavior by using storage internal to the RNN to process input data sequences. Various steps in the flow 800 may be changed in order, repeated, omitted, or the like without departing from the disclosed concepts. Various embodiments of the flow 800 can be included in a computer program product embodied in a non-transitory computer readable medium that includes code executable by one or more processors.

Figure 9:
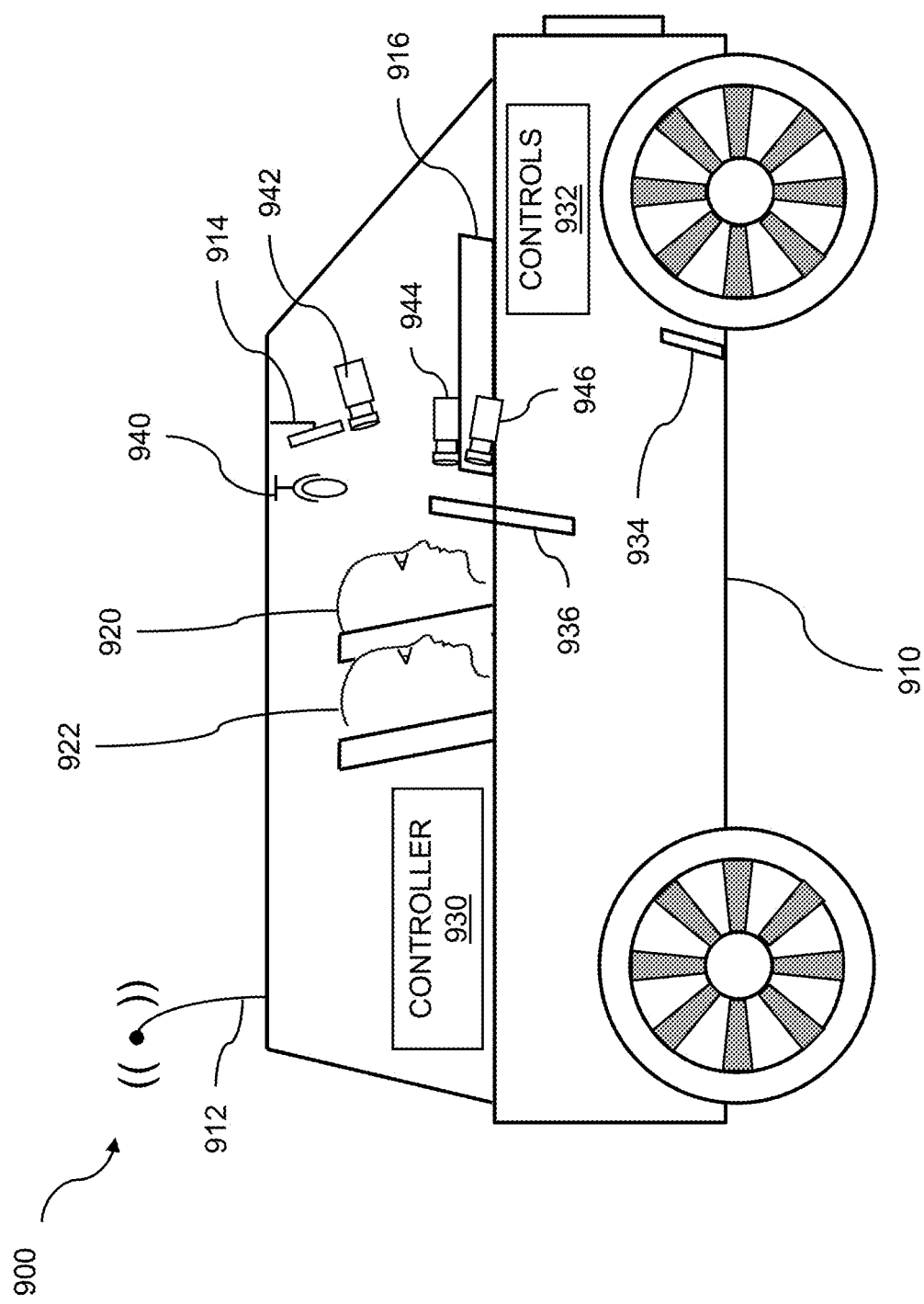
FIG. 9 is a system diagram for an interior of a vehicle.

FIG. 9 is a system diagram for an interior of a vehicle 900. Personal emotional profile generation can be used for vehicle manipulation. Cognitive state data is obtained from an individual. Processors are used to extract the cognitive state data from facial images of an individual captured as they respond to stimuli within a vehicle. The cognitive state data extracted from facial images is analyzed to produce cognitive state information. The cognitive state information of the individual is correlated with cognitive state information from a plurality of people. The cognitive state information is augmented based on audio data collected from within the vehicle contemporaneously with the facial images. Processors are used to categorize the individual with others from the plurality of people based on the correlating and the augmenting, and the vehicle is manipulated based on both the cognitive state information that was augmented and the categorizing. One or more occupants of a vehicle 910, such as occupants 920 and 922, can be observed using a microphone 940, one or more cameras 942, 944, or 946, and other audio and image capture techniques. The image data can include video data. The video data and the audio data can include cognitive state data, where the cognitive state data can include facial data, voice data, physiological data, and the like. The occupant 920 can be a driver of the vehicle 910, a passenger 922 within the vehicle, and so on.

The cameras or imaging devices that can be used to obtain images including facial data from the occupants of the vehicle 910 can be positioned to capture the face of the vehicle operator, the face of a vehicle passenger, multiple views of the faces of occupants of the vehicle, and so on. The cameras can be located near a rear-view mirror 914 such as camera 942, positioned near or on a dashboard 916 such as camera 944, positioned within the dashboard such as camera 946, and so on. The microphone or audio capture device 940 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 910 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 910 can include standard controls such as a steering wheel 936, a throttle control (not shown), a brake 934, and so on. The interior of the vehicle can include other controls 932 such as controls for seats, mirrors, climate settings, audio systems, etc. The controls 932 of the vehicle 910 can be controlled by a controller 930. The controller 930 can control the vehicle 910 in various manners such as autonomously, semi-autonomously, assertively to a vehicle occupant 920 or 922, etc. In embodiments, the controller provides vehicle control or manipulation techniques, assistance, etc. The controller 930 can receive instructions via an antenna 912 or using other wireless techniques. The controller 930 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest route, and so on.

Figure 10:
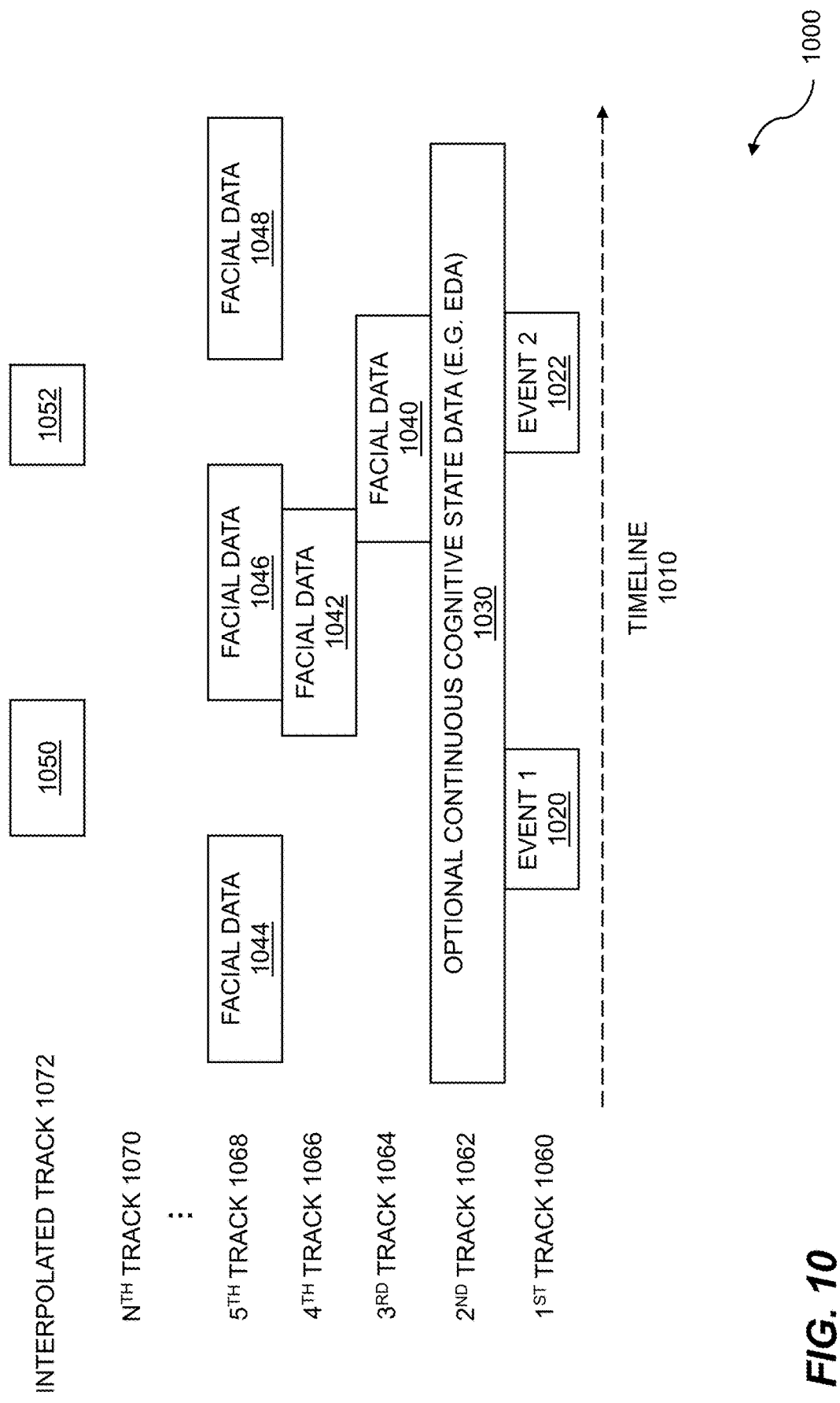
FIG. 10 is a timeline with information tracks relating to cognitive states.

FIG. 10 is a timeline with information tracks relating to cognitive states. A timeline can show one or more cognitive states that can be experienced by a vehicle occupant. The vehicle occupant can be an operator of the vehicle, a passenger of the vehicle, a custodial operation of the vehicle, and so on. The timeline can be based on personal emotional profile generation for vehicle manipulation. An individual's images including facial images are obtained, and cognitive state data is extracted from the images. The cognitive state data is analyzed to produce cognitive state information. The cognitive state information of the individual is correlated with that of other people, and is augmented with cognitive state information from collected audio data. The individual is categorized with other people, and the vehicle is manipulated based on the augmenting and the categorizing.

The timeline 1010 with information tracks 1000 relates to various cognitive states. A first track 1060 shows events that, in embodiments, are related to use of a computer by the individual. A first event 1020 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 1060. A second event 1022 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 1062 can include continuously collected cognitive state data such as electrodermal activity data 1030. A third track 1064 can include facial data. The facial data can be collected intermittently when the individual is looking toward a camera. The facial data 1040 can include one or more still photographs, videos, or abstracted facial expressions which can be collected when the user looks in the direction of the camera. A fourth track 1066 can include facial data that is collected either intermittently or continuously by a second camera. The facial data 1042 can include one or more still photographs, videos, or abstracted facial expressions which can be collected when the user looks in the direction of that camera. A fifth track 1068 can include facial data that is collected from a third camera, such as the webcam. In the example shown, the fifth track 1068 includes first facial data 1044, second facial data 1046, and third facial data 1048, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the $n^{th}$ track 1070, of cognitive state data of any type can be collected. The additional tracks 1070 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 1072 can be included and can be associated with cognitive state data that is collected on an intermittent basis, such as the facial data of the fifth track 1068. Interpolated data 1050 and further interpolated data 1052 can contain interpolations of the facial data of the fifth track 1068 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 1030 and/or any of the collected facial data 1040, 1042, 1044, 1046, and 1048, can be tagged. The tags can include metadata related to the cognitive state data, including, but not limited to, the device that collected the cognitive state data; the individual from whom the cognitive state data was collected; the task being performed by the individual; the media being viewed by the individual; and the location, environcognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such the tags can be used locally on the machine where the cognitive state data was collected and/or remotely on a remote server or a cloud/web service.

Other tags can be related to the cognitive state data. Further embodiments can include tagging the cognitive state data with sensor data. The sensor data can be obtained from the vehicle occupant along with the obtaining of the video data or the audio data, instead of the video data or the audio data, etc. In embodiments, the sensor data can include one or more of vehicle interior temperature, vehicle exterior temperature, time of day, day of week, season, level of daylight, weather conditions, road conditions, traffic conditions, headlight activation, windshield wiper activation, vehicle settings, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 11:
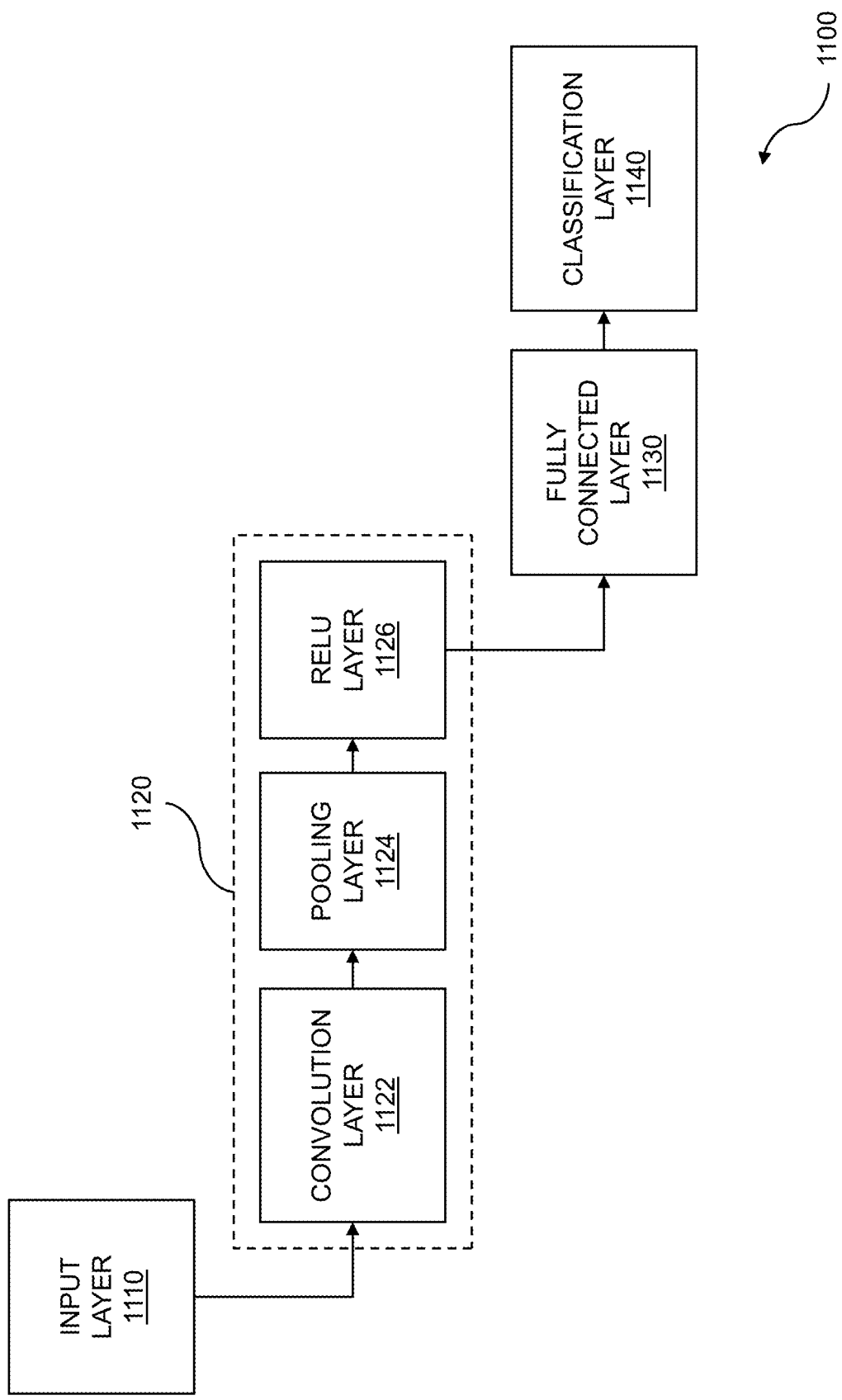
FIG. 11 is an example showing a convolutional neural network (CNN).

FIG. 11 is an example showing a convolutional neural network (CNN). A convolutional neural network such as 1100 can be used for deep learning, where the deep learning can be applied to personal emotional profile generation for vehicle manipulation. Cognitive state data is extracted from facial images obtained from an individual, and cognitive state information is produced by analyzing the data. The cognitive state information is correlated with cognitive state information from other people, and is augmented based audio data. The individual is categorized with the other people, and the vehicle is manipulated based on the augmenting and the categorizing. The convolutional neural network can be applied to tasks such as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 11 is an example showing a convolutional neural network 1100. The convolutional neural network can be used for deep learning, where the deep learning can be applied to cognitive state-based vehicle manipulation using near-infrared image processing. The deep learning system can be accomplished using a convolution neural network or other techniques. The deep learning can accomplish facial recognition and analysis tasks. The network includes an input layer 1110. The input layer 1110 receives image data. The image data can be input in a variety of formats, such as JPEG, TIFF, BMP, and GIF. Compressed image formats can be decompressed into arrays of pixels, wherein each pixel can include an RGB tuple. The input layer 1110 can then perform processing such as identifying boundaries of the face, identifying landmarks of the face, extracting features of the face, and/or rotating a face within the plurality of images.

The network includes a collection of intermediate layers 1120. The multilayered analysis engine can include a convolutional neural network. Thus, the intermediate layers can include a convolution layer 1122. The convolution layer 1122 can include multiple sublayers, including hidden layers, within it. The output of the convolution layer 1122 feeds into a pooling layer 1124. The pooling layer 1124 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1124. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (ReLU) layer 1126. The output of the pooling layer 1124 can be input to the ReLU layer 1126. In embodiments, the ReLU layer implements an activation function such as $f(x)=\max(0,x)$, thus providing an activation with a threshold at zero. In some embodiments, the ReLU layer 1126 is a leaky ReLU layer. In this case, instead of the activation function providing zero when x<0, a small negative slope is used, resulting in an activation function such as $f(x)=1(x<0)(\alpha x)+1(x>=0)(x)$. This can reduce the risk of "dying ReLU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1122 and one or more hidden layers, and wherein the multilayered analysis engine can be used for emotional analysis.

The example 1100 includes a fully connected layer 1130. The fully connected layer 1130 processes each pixel/data point from the output of the collection of intermediate layers 1120. The fully connected layer 1130 takes all neurons in the previous layer and connects them to every single neuron it has. The output of the fully connected layer 1130 provides input to a classification layer 1140. The output of the classification layer 1140 provides a facial expression and/or cognitive state as its output. Thus, a multilayered analysis engine such as the one depicted in FIG. 11 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt, or learn, as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 12:
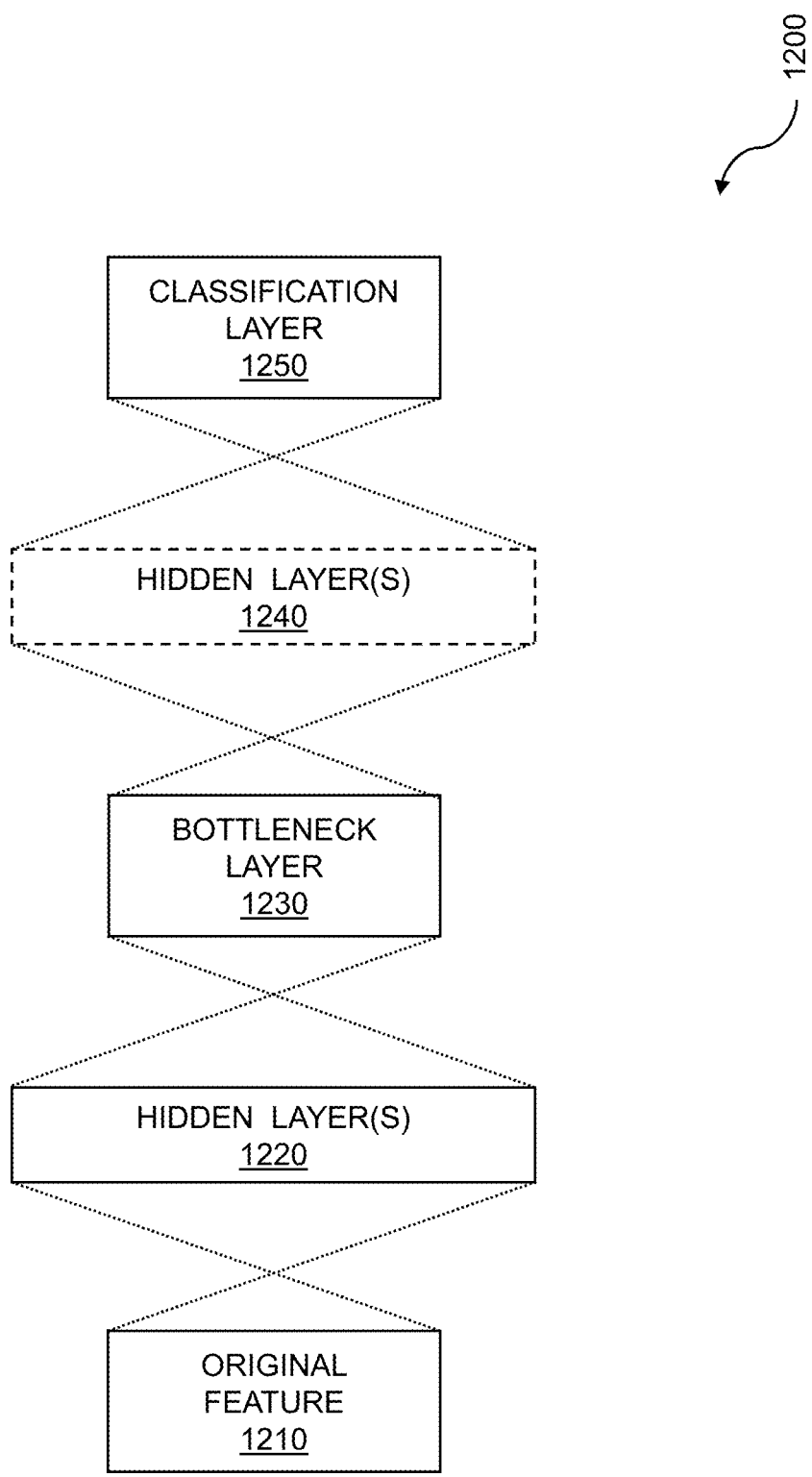
FIG. 12 illustrates a bottleneck layer within a deep learning environment.

FIG. 12 illustrates a bottleneck layer within a deep learning environment. A plurality of layers in a deep neural network (DNN) can include a bottleneck layer. The bottleneck layer can be used for personal emotional profile generation for vehicle manipulation. A deep neural network can apply classifiers such as image classifiers, facial classifiers, audio classifiers, speech classifiers, physiological classifiers, and so on. The classifiers can be learned by analyzing cognitive state data. Cognitive state data is extracted from facial images of an individual. The cognitive state data is analyzed to produce cognitive state information. The cognitive state information is augmented with audio data, and the cognitive state information is correlated with the cognitive state information from other people. The individual is categorized with other people, and the vehicle is manipulated based on the augmenting and the categorizing.

Layers of a deep neural network can include a bottleneck layer 1200. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1210. A feature such as an image feature can include points, edges, objects, boundaries between and among regions, properties, and so on. The deep neural network can include one or more hidden layers 1220. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1230. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1240. The number of the hidden layers can include zero hidden layers, one hidden layer, a plurality of hidden layers, and so on. The hidden layers following the bottleneck layer can include more nodes than the bottleneck layer. The deep neural network can include a classification layer 1250. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 13:
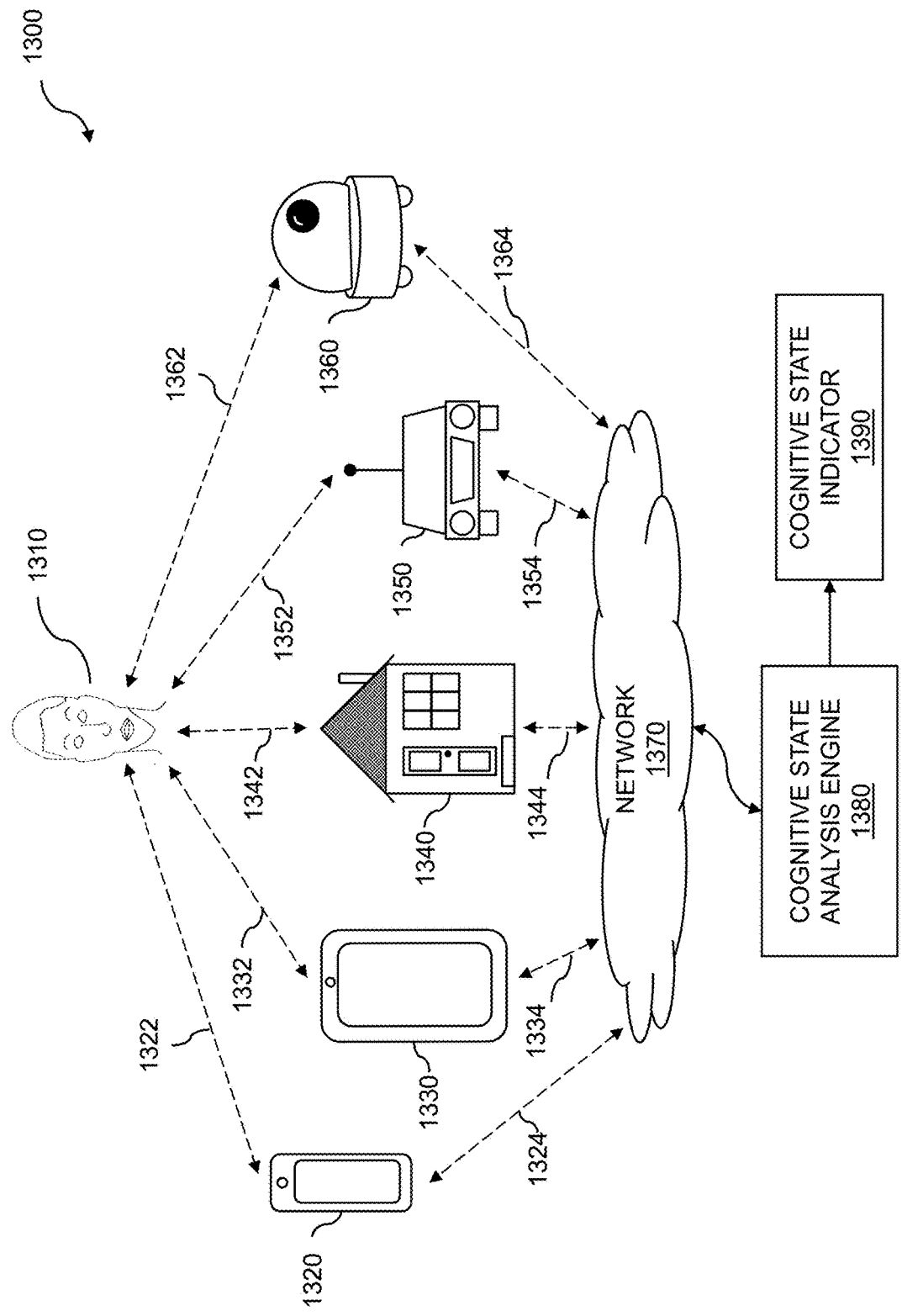
FIG. 13 shows data collection including devices and locations.

FIG. 13 shows data collection including devices and locations 1300. Data, including video data, audio data and physiological data, can be obtained for personal emotional profile generation for vehicle manipulation. The data can be obtained from multiple devices, vehicles, and locations. Cognitive state data, which is extracted from facial images of an individual, is analyzed to produce cognitive state information. The cognitive state information is augmented with audio data collected contemporaneously with the facial images. The individual's cognitive state information is correlated and categorized with cognitive state information of other people. The vehicle is manipulated based on the augmented and categorized cognitive state information.

The multiple mobile devices, vehicles, and locations 1300 can be used separately or in combination to collect video data on a user 1310. The video data can include facial data. Other data such as audio data, physiological data, and so on, can be collected on the user. While one person is shown, the video data, or other data, can be collected on multiple people. A user 1310 can be observed as she or he is performing a task, experiencing an event, viewing a media presentation, and so on. The user 1310 can be shown one or more media presentations, political presentations, social media, or another form of displayed media. The one or more media presentations can be shown to a plurality of people. The media presentations can be displayed on an electronic display coupled to a client device. The data collected on the user 1310 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1310 can be analyzed and viewed for a variety of purposes including expression analysis, mental state analysis, cognitive state analysis, and so on. The electronic display can be on a smartphone 1320 as shown, a tablet computer 1330, a personal digital assistant, a television, a mobile monitor, or any other type of electronic device. In one embodiment, expression data is collected on a mobile device such as a cell phone 1320, a tablet computer 1330, a laptop computer, or a watch. Thus, the multiple sources can include at least one mobile device, such as a phone 1320 or a tablet 1330, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1310, data can be collected in a house 1340 using a web camera or the like; in a vehicle 1350 using a web camera, client device, etc.; by a social robot 1360, and so on.

As the user 1310 is monitored, the user 1310 might move due to the nature of the task, boredom, discomfort, distractions, or for another reason. As the user moves, the camera with a view of the user's face can be changed. Thus, as an example, if the user 1310 is looking in a first direction, the line of sight 1322 from the smartphone 1320 is able to observe the user's face, but if the user is looking in a second direction, the line of sight 1332 from the tablet 1330 is able to observe the user's face. Furthermore, in other embodiments, if the user is looking in a third direction, the line of sight 1342 from a camera in the house 1340 is able to observe the user's face, and if the user is looking in a fourth direction, the line of sight 1352 from the camera in the vehicle 1350 is able to observe the user's face. If the user is looking in a fifth direction, the line of sight 1362 from the social robot 1360 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1310 can also use a wearable device including a camera for gathering contextual information and/or collecting expression data on other users. Because the user 1310 can move her or his head, the facial data can be collected intermittently when she or he is looking in a direction of a camera. In some cases, multiple people can be included in the view from one or more cameras, and some embodiments include filtering out faces of one or more other people to determine whether the user 1310 is looking toward a camera. All or some of the expression data can be continuously or sporadically available from the various devices and other devices.

The captured video data can include cognitive content, such as facial expressions, etc., and can be transferred over a network 1370. The network can include the Internet or other computer network. The smartphone 1320 can share video using a link 1324, the tablet 1330 using a link 1334, the house 1340 using a link 1344, the vehicle 1350 using a link 1354, and the social robot 1360 using a link 1364. The links 1324, 1334, 1344, 1354, and 1364 can be wired, wireless, and hybrid links. The captured video data, including facial expressions, can be analyzed on a cognitive state analysis engine 1380, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1390. The cognitive state indicator 1390 can indicate cognitive states, mental states, moods, emotions, etc. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 14:
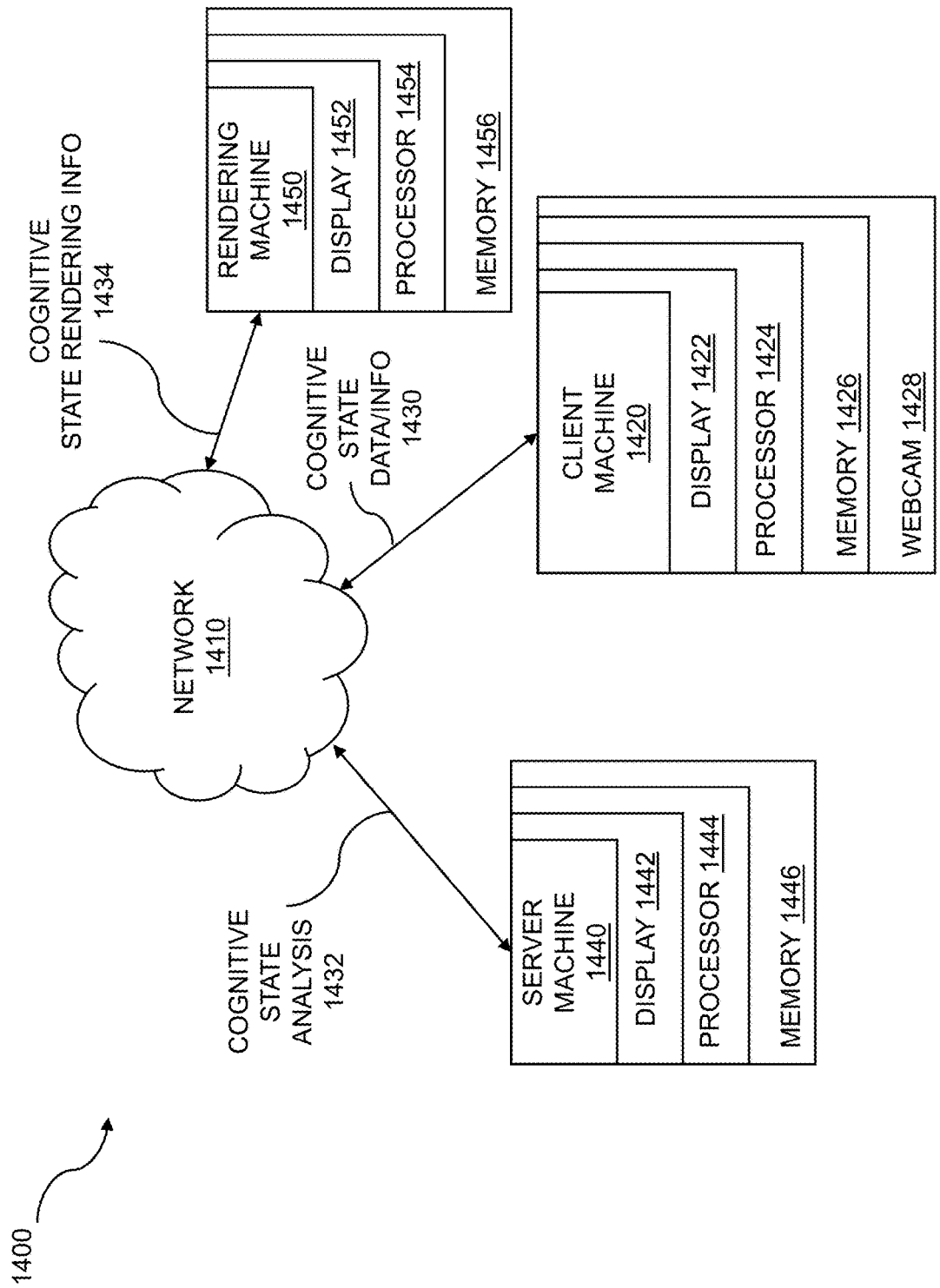
FIG. 14 is a system for personal emotional profile usage.

FIG. 14 is a system diagram for personal emotional profile generation and usage. The system 1400 can comprise a computer system for cognitive state analysis comprising: a memory which stores instructions; one or more processors attached to the memory wherein the one or more processors, when executing the instructions which are stored, are configured to: obtain cognitive state data from an individual within a vehicle, wherein the cognitive state data is extracted, using one or more processors, from facial images of the individual that are captured as the individual responds to stimuli; analyze the cognitive state data extracted from facial images to produce cognitive state information; categorize, using one or more processors, the cognitive state information against a personal emotional profile for the individual; and manipulate the vehicle, based on the cognitive state information, the categorizing, and the stimuli.

The system 1400 can include one or more client machines 1420 linked to an analysis server 1440 via a network 1410 such as the Internet or another computer network. The client machine 1420 can include one or more processors 1424 coupled to a memory 1426 which can store and retrieve instructions, a display 1422, and a webcam 1428. The display 1422 can be any electronic display, including but not limited to a computer display, a laptop screen, a net-book screen, a tablet computer screen, a cell phone display, a mobile device display, a remote with a display, a television, a projector, or the like. The webcam 1428 can comprise a video camera, a still camera, a thermal imager, a CCD device, a phone camera, a three-dimensional camera, a depth camera, multiple webcams used to show different views of a person, or any other type of image capture apparatus that allows captured data to be used in an electronic system. In embodiments, the analysis server 1440 includes one or more processors 1444 coupled to a memory 1446 which can store and retrieve instructions, and can also include a display 1442.

In some embodiments, the rendering of emotional status can occur on a different computer than the client machine 1420 or the analysis server 1440. This computer can include a rendering machine 1450 which can receive cognitive state analysis 1432 from the analysis machine 1440, cognitive state data 1430 from the client machine 1420, or both. The data received by the rendering machine 1450 can be considered cognitive state rendering information 1434. In embodiments, the rendering machine 1450 includes one or more processors 1454 coupled to a memory 1456 which can store and retrieve instructions, and can include a display 1452.

The analysis server 1440 can receive the cognitive state data and analyze the cognitive state data to produce emotional status information, so that the analyzing of the cognitive state data can be performed by a web service. The analysis server 1440 can use the cognitive state information received from the client machine 1420 or produced from the cognitive state data to analyze an individual's emotional profile. In some embodiments, the analysis server 1440 receives cognitive state data and/or cognitive state information from a plurality of client machines, and aggregates the cognitive state information for use in optimizing the emotional status of an individual or plurality of individuals. In at least one embodiment, the client machine, analysis server, and/or rendering functions can be accomplished by one computer.

In embodiments, a computer program product embodied in a non-transitory computer readable medium for cognitive state analysis, the computer program product comprising code which causes one or more processors to perform operations of: obtaining cognitive state data from an individual within a vehicle, wherein the cognitive state data is extracted, using one or more processors, from facial images of the individual that are captured as the individual responds to stimuli; analyzing the cognitive state data extracted from facial images to produce cognitive state information; categorizing, using one or more processors, the cognitive state information against a personal emotional profile for the individual; and manipulating the vehicle, based on the cognitive state information, the categorizing, and the stimuli.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples but is to be understood in the broadest sense allowable by law.

What is claimed is:

1. A computer-implemented method for cognitive state analysis comprising:
   obtaining cognitive state data from an individual within a vehicle, wherein the cognitive state data is extracted, using one or more processors, from facial images of the individual that are captured as the individual responds to stimuli;
   analyzing the cognitive state data extracted from facial images to produce cognitive state information;
   developing norms for the individual;
   categorizing, using one or more processors, the cognitive state information against a personal emotional profile for the individual; and manipulating the vehicle, based on the cognitive state information, the categorizing, and the stimuli.

2. The method of claim 1 wherein the personal emotional profile is generated by comparing the cognitive state information of the individual with cognitive state norms from a plurality of individuals.

3. The method of claim 1 wherein the personal emotional profile is generated based on cognitive state data for the individual that is accumulated over time.

4. The method of claim 3 wherein the personal emotional profile is further generated based on two or more vehicle journeys by the individual.

5. The method of claim 4 wherein at least two of the two or more vehicle journeys are accomplished in two or more vehicles.

6. The method of claim 1 wherein the stimuli occurs within the vehicle.

7. The method of claim 1 wherein the stimuli occurs outside of the vehicle.

8. The method of claim 1 further comprising pushing media content to the individual based on the categorizing.

9. The method of claim 1 wherein the categorizing is based on a plurality of expressions by the individual.

10. The method of claim 9 wherein the categorizing is further based on a rate of change in the plurality of expressions by the individual.

11. The method of claim 1 wherein the personal emotional profile further comprises off-line behavior.

12. The method of claim 1 further comprising correlating a component of the personal emotional profile to a purchase intent.

13. The method of claim 1 further comprising using the personal emotional profile to predict future reactions to stimuli.

14. The method of claim 1 further comprising using the personal emotional profile to categorize digital media.

15. The method of claim 1 further comprising matching the individual with one or more people from a plurality of people, based on the categorizing.

16. The method of claim 1 wherein the cognitive state data is collected while the individual views a collection of digital media.

17. The method of claim 16 wherein the cognitive state information from a plurality of people is based on the plurality of people viewing the collection of digital media.

18. The method of claim 1 further comprising using response differences in the individual, over an interval of time, from the norms for the individual to make a recommendation.

19. The method of claim 1 further comprising developing norms for a demographic group.

20. The method of claim 19 further comprising using response differences for the individual from the norms for the demographic group to refine a profile.

21. The method of claim 1 further comprising augmenting the cognitive state information based on audio data collected from within the vehicle, wherein the audio data is collected contemporaneously with the facial images.

22. The method of claim 21 wherein the audio data includes speech.

23. The method of claim 21 wherein the audio data includes non-speech vocalizations.

24. The method of claim 1 further comprising tagging the cognitive state data with sensor data.

25. The method of claim 24 wherein the sensor data includes one or more of vehicle interior temperature, vehicle exterior temperature, time of day, day of week, season, level of daylight, weather conditions, road conditions, traffic conditions, headlight activation, windshield wiper activation, vehicle settings, entertainment center selection, or entertainment center volume.

26. The method of claim 1 wherein the manipulating is based on a deviation from the norms.

27. A computer program product embodied in a non-transitory computer readable medium for cognitive state analysis, the computer program product comprising code which causes one or more processors to perform operations of:
obtaining cognitive state data from an individual within a vehicle, wherein the cognitive state data is extracted, using one or more processors, from facial images of the individual that are captured as the individual responds to stimuli;
analyzing the cognitive state data extracted from facial images to produce cognitive state information;
developing norms for the individual;
categorizing, using one or more processors, the cognitive state information against a personal emotional profile for the individual; and
manipulating the vehicle, based on the cognitive state information, the categorizing, and the stimuli.

28. A computer system for cognitive state analysis comprising:
a memory which stores instructions;
one or more processors attached to the memory wherein the one or more processors, when executing the instructions which are stored, are configured to:
obtain cognitive state data from an individual within a vehicle, wherein the cognitive state data is extracted, using one or more processors, from facial images of the individual that are captured as the individual responds to stimuli;
analyze the cognitive state data extracted from facial images to produce cognitive state information;
develop norms for the individual;
categorize, using one or more processors, the cognitive state information against a personal emotional profile for the individual; and
manipulate the vehicle, based on the cognitive state information, the categorizing, and the stimuli.

* * * * *